United States Patent
Sørensen et al.

(10) Patent No.: US 9,370,193 B2
(45) Date of Patent: Jun. 21, 2016

(54) ENZYMATIC GENERATION OF FUNCTIONAL LIPIDS FROM CEREALS OR CEREAL BI-STREAMS

(75) Inventors: Jens Frisbaek Sørensen, Arhus N (DK); René Mikkelsen, Skanderborg (DK); Charlotte Horsmans Poulsen, Brabrand (DK); Karsten Matthias Kragh, Viby J (DK)

(73) Assignee: DUPONT NUTRITION BIOSCIENCES APS (DK)

( * ) Notice: Subject to any disclaimer, the term of this patent is extended or adjusted under 35 U.S.C. 154(b) by 72 days.

(21) Appl. No.: 13/144,588

(22) PCT Filed: Jan. 15, 2010

(86) PCT No.: PCT/EP2010/050445
§ 371 (c)(1),
(2), (4) Date: Jul. 14, 2011

(87) PCT Pub. No.: WO2010/081869
PCT Pub. Date: Jul. 22, 2010

(65) Prior Publication Data
US 2012/0003690 A1 Jan. 5, 2012

Related U.S. Application Data

(60) Provisional application No. 61/145,366, filed on Jan. 16, 2009, provisional application No. 61/147,412, filed on Jan. 26, 2009.

(30) Foreign Application Priority Data

Jan. 16, 2009 (EP) ..................... 09150744
Jan. 26, 2009 (EP) ..................... 09151352
Apr. 1, 2009 (EP) ..................... 09157090

(51) Int. Cl.
*C12N 9/18* (2006.01)
*C12N 9/20* (2006.01)
*C12Q 1/37* (2006.01)
*C12Q 1/40* (2006.01)
*A21D 8/04* (2006.01)
*A23L 1/10* (2006.01)
*A23L 1/105* (2006.01)
*C11B 1/02* (2006.01)

(52) U.S. Cl.
CPC .............. *A21D 8/042* (2013.01); *A23L 1/1016* (2013.01); *A23L 1/1055* (2013.01); *C11B 1/025* (2013.01); *C12Y 302/01001* (2013.01); *C12Y 302/0102* (2013.01); *C12Y 302/01002* (2013.01); *C12Y 302/01003* (2013.01); *C12Y 302/01004* (2013.01); *C12Y 302/0106* (2013.01); *C12Y 302/01008* (2013.01); *C12Y 302/01015* (2013.01); *C12Y 302/01021* (2013.01); *C12Y 302/01024* (2013.01); *C12Y 302/01041* (2013.01); *C12Y 302/01055* (2013.01); *C12Y 302/01068* (2013.01); *C12Y 302/01089* (2013.01); *C12Y 302/01091* (2013.01); *C12Y 302/01133* (2013.01)

(58) Field of Classification Search
None
See application file for complete search history.

(56) References Cited

U.S. PATENT DOCUMENTS

| | | | |
|---|---|---|---|
| 6,365,204 B1 | 4/2002 | Spendler et al. | |
| 2002/0009518 A1* | 1/2002 | Soe | 426/33 |
| 2006/0078648 A1* | 4/2006 | De Kreij et al. | 426/49 |

FOREIGN PATENT DOCUMENTS

| | | |
|---|---|---|
| CN | 1675355 A | 9/2005 |
| EP | 0 468 731 A1 | 1/1992 |
| EP | 0 585 988 A1 | 3/1994 |
| EP | 0 659 049 B1 | 3/2001 |
| EP | 1 193 314 A1 | 4/2002 |
| EP | 0 977 869 B1 | 7/2004 |
| WO | WO 94/04035 A1 | 3/1994 |
| WO | WO 98/45453 A1 | 10/1998 |
| WO | WO 00/32758 A1 | 6/2000 |
| WO | WO 01/39602 A1 | 6/2001 |
| WO | WO 02/094123 A2 | 11/2002 |
| WO | WO 2004018660 A2 | 3/2004 |
| WO | WO 2005/079193 A2 | 9/2005 |
| WO | WO 2008/112282 A1 | 9/2008 |

OTHER PUBLICATIONS

Park et al., Cereal Chemistry, 2006, vol. 83, No. 6, p. 611-616, Abstract Only.*
Galliard et al., Journal of Cereal Science, 1988, vol. 8, No. 2, p. 147-154.*
Castello et al., Cereal Grain, 1999, vol. 76, No. 4, p. 476-482.*
Kaur et al., Biotechnology Letters, 1993, vol. 15, No. 3 p. 257-262.*
Hernandez et al., JAOCS, 2000, vol. 77, No. 2, p. 177-180.*
Ukai et al., Food Chemistry, 2007, vol. 102, p. 225-231.*
De Maria et al., Appl Microbiol Biotechnol, 2007, vol. 74, p. 290-300.*
Hemavathy et al., JAOCS, 1987, vol. 64, No. 7, p. 1016-1019.*

(Continued)

*Primary Examiner* — Kade Ariani

(57) ABSTRACT

The present invention relates to the modification of lipids in lipid-containing plant material, such as cereal bran for the generation of functional lipids. The present invention further relates to the preparation of compositions comprising such functional lipids as well as the use of these compositions comprising functional lipids and other functional compounds derived from the action of lipid modifying enzymes for the preparation of composition suitable for the preparation of bio-ethanol as well as food products, such as bread.

25 Claims, 9 Drawing Sheets

(56) References Cited

OTHER PUBLICATIONS

Figure 1:
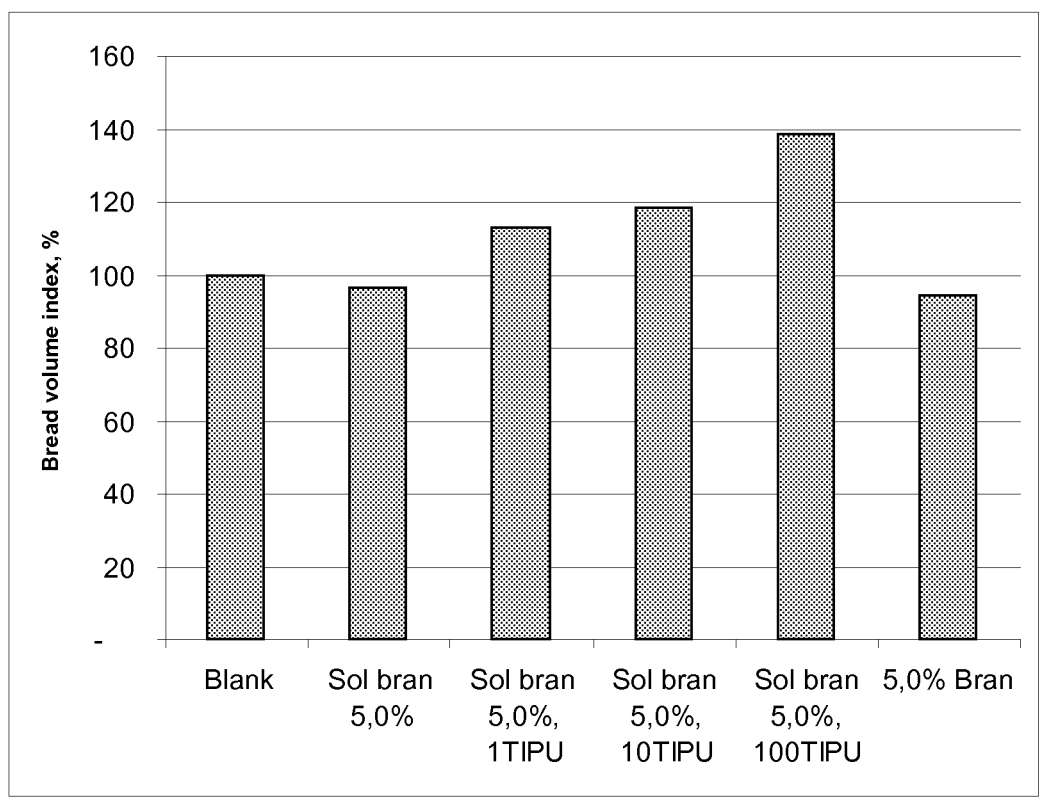

Morrison, W., et al., "Distribution of Soft Wheat Kernel Lipids into Flour Milling Fractions," *J. Sci. Food Agric.*, 1981, vol. 32, pp. 579-587.

Novozymes A/S, "Combined use of glucose oxidase and phospholipase for baking," Research Disclosure 442055, 2001, Mason Publications, Hampshire, GB, 1 page.

Swain, B., et al., "Cost benefit analysis of broilers on diet incorporated with autoclaved high fibre ingredients and enzyme feed supplement," *Indian Journal of Poultry Science*, 1999, vol. 34(3), pp. 400-402—Abstract Only, Database Accession No. PREV200300207825.

Hendrick, J.A., et al., "Various Dietary Fibers Have Different Effects on Lipase-Catalyzed Hydrolysis of Tributyrin in Vitro," *J. Nutr.*, 1992, vol. 122, No. 2, pp. 269-277.

Laurikainen, T., et al., "Effects of Enzymes in Fibre-Enriched Baking," *J. Sci. Food Agric.*, 1998, vol. 76, No. 2, pp. 239-249.

O'Connor, C.J., et al., "The Inhibitory Effects of Brans and Their Aqueous Extracts on the Lipolysis of Tributyrin Catalyzed by Calf Pregastric Lipase," *J. Food Sci.*, 2003, vol. 68, No. 5, pp. 1818-1825.

Anonymous, "Chapter 4 Nutrient Composition and Digestibility of DDGS: Variability and In Vitro Measurement Introduction," *DDGS User Handbook*, 2012, pp. 1-22, XP55158638, Retrieved from the Internet: URL:http://www.grains.org/sites/default/files/ddgs-handbook/Chapter-4.pdf [Retrieved on Dec. 15, 2014].

Communication from European Patent Office for European Patent Application No. 10700862.5 dated Dec. 22, 2014.

Katina, K., et al., "Effects of sourdough and enzymes on staling of high-fibre wheat bread," *LWT*, 2006, vol. 39, pp. 479-491.

* cited by examiner

ENZYMATIC GENERATION OF FUNCTIONAL LIPIDS FROM CEREALS OR CEREAL BI-STREAMS

CROSS-REFERENCE TO RELATED APPLICATIONS

This application is the U.S. National Stage of International Application PCT/EP2010/050445 filed Jan. 15, 2010, which designates the U.S and was published by the International Bureau in English on Jul. 22, 2010, and which claims the benefit of European Patent Application No. 09150744.2, filed Jan. 16, 2009, U.S. Provisional Application No. 61/145,366, filed Jan. 16, 2009, European Patent Application No. 09151352.3, filed Jan. 26, 2009, U.S. Provisional Application No. 61/147,412, filed Jan. 26, 2009, and European Patent Application No. 09157090.3, filed Apr. 1, 2009, all of which are hereby incorporated herein in their entirety by reference.

FIELD OF THE INVENTION

The present invention relates to the modification of lipids in lipid-containing plant material, such as cereal bran for the generation of functional lipids. The present invention further relates to the preparation of compositions comprising such functional lipids as well as the use of these compositions comprising functional lipids and other functional compounds derived from the action of lipid modifying enzymes for the preparation of composition suitable for the preparation of bio-ethanol as well as food products, such as bread.

BACKGROUND OF THE INVENTION

Utilization of sidestreams from processing of plant materials fermentation residues, such as cereal bran from milling or Distillers dried spent grain with solubles (DDGS) has received little attention beyond use in animal feeds.

The beneficial use of lipolytic enzymes (E.G. 3.1.1.x) in food and/or feed industrial applications has been known for many years.

However most of the prior art describes the use of lipolytic enzymes in flour and in dough and not for sidestreams or by-products of industrial processes. For instance, in EP 0 585 988 it is claimed that lipase addition to dough resulted in an improvement in the antistaling effect. WO94/04035 teaches that an improved bread softness can be obtained by adding a lipase to dough without the addition of any additional fat/oil to the dough.

The substrate for lipases in plant material is a complex mixture of polar and non-polar lipids. The polar lipids can be divided into glycolipids and phospholipids. These lipids are built up of glycerol esterified with two fatty acids and a polar group. The polar group contributes to surface activity of these lipids.

Enzymatic cleavage of one of the fatty acids in these lipids leads to lipids with a much higher surface activity. It is well known that emulsifiers, such as DATEM, with high surface activity are very functional when added to dough.

Lipolytic enzymes hydrolyse one or more of the fatty acids from lipids present in the plant material which can result in the formation of powerful emulsifier molecules.

In EP 1 193 314, the inventors discovered that the use of lipolytic enzymes active on glycolipids was particularly beneficial in applications in bread making.

Morrison et al. J. Sci. Food Agric, 1981, 32, 579-587 disclose the distribution of soft wheat kernel lipids in the flour milling fractions.

There is a need in the art for better utilisation of sidestreams from processing of plant materials, such as cereal bran from milling, soap stocks from refining of vegetable oils, Distillers dried spent grain with solubles (DDGS), wherein less of the plant material will go to low price applications like cattle feed. Furthermore, it is a long felt need to be able to utilise the bran fraction from cereals in traditionally, already existing cereal products, without significant impact on the product appearance/structure, the color or the taste, and to make it possible to increase the health and nutritional effect of already existing products.

OBJECT OF THE INVENTION

It is an object of the present invention to provide methods for generating functional lipids from plant material in general and from industrial side-streams in particular. It is furthermore an object of the present invention to provide suitable methods enabling the utilisation of compositions comprising functional lipids derived from plant material, such as bran in traditionally, in food products, such as in bread or cereal products, without significant impact on the product appearance/structure, the color or the taste, and to make it possible to increase the health and nutritional effect of already existing products.

SUMMARY OF THE INVENTION

In a broad aspect the present invention relates to methods for treating plant material containing lipids with lipid modifying enzymes, for the generation of modified lipids, such as functional lipids from plant materials.

In a first aspect the present invention relates to a method for the treatment of lipid-containing plant material, the method comprising the step of treating a liquid suspension of an at least partly solubilised lipid-containing plant material with one or more lipid modifying enzyme.

In a second aspect the present invention relates to a composition comprising lipids and/or modified lipids, such as functional lipid produced by a method for the treatment of lipid-containing plant material, the method comprising the step of treating a liquid suspension of an at least partly solubilised lipid-containing plant material with one or more lipid modifying enzyme.

In a third aspect the present invention relates to the use of a composition comprising lipids and/or modified lipids, such as functional lipid produced by a method for the treatment of lipid-containing plant material, the method comprising the step of treating a liquid suspension of an at least partly solubilised lipid-containing plant material with one or more lipid modifying enzyme, the use being for the production of a food product.

In a further aspect the present invention relates to the use of a composition comprising lipids and/or modified lipids, such as functional lipid produced by a method for the treatment of lipid-containing plant material, the method comprising the step of treating a liquid suspension of an at least partly solubilised lipid-containing plant material with one or more lipid modifying enzyme, the use being for the production of bio-ethanol.

In a further aspect the present invention relates to a food product obtained by the use of a composition comprising lipids and/or modified lipids, such as functional lipid produced by a method for the treatment of lipid-containing plant material, the method comprising the step of treating a liquid suspension of an at least partly solubilised lipid-containing plant material with one or more lipid modifying enzyme.

In a further aspect the present invention relates to a bioethanol obtained by the use of a composition comprising lipids and/or modified lipids, such as functional lipid produced by a method for the treatment of lipid-containing plant material, the method comprising the step of treating a liquid suspension of an at least partly solubilised lipid-containing plant material with one or more lipid modifying enzyme.

In a further aspect the present invention relates to a kit of parts comprising
- a) a combination of enzymes comprising: one or more lipid modifying enzyme; one or more cell-wall modifying enzyme, and optionally one or more further enzyme;
- b) instructions for use in a method according to the invention; and
- c) Optionally other ingredients for the preparation of a food product.

LEGENDS TO THE FIGURE

FIG. 1. Baking trial results. Rel vol of breads versus blank (%). The columns represent the bread volume for trial numbers 1-6 according to table 5 and 6.

Figure 2:
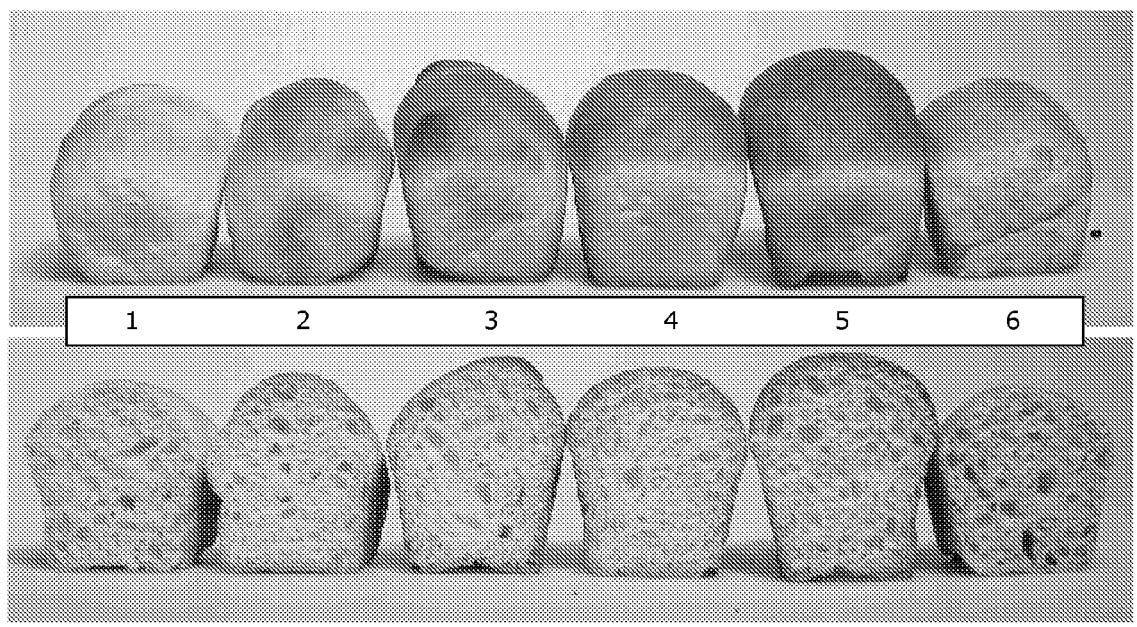

FIG. 2. Breads obtained from baking with soluble bran fractions obtained. Numbers refer to numbers in table 5.

Figure 3:
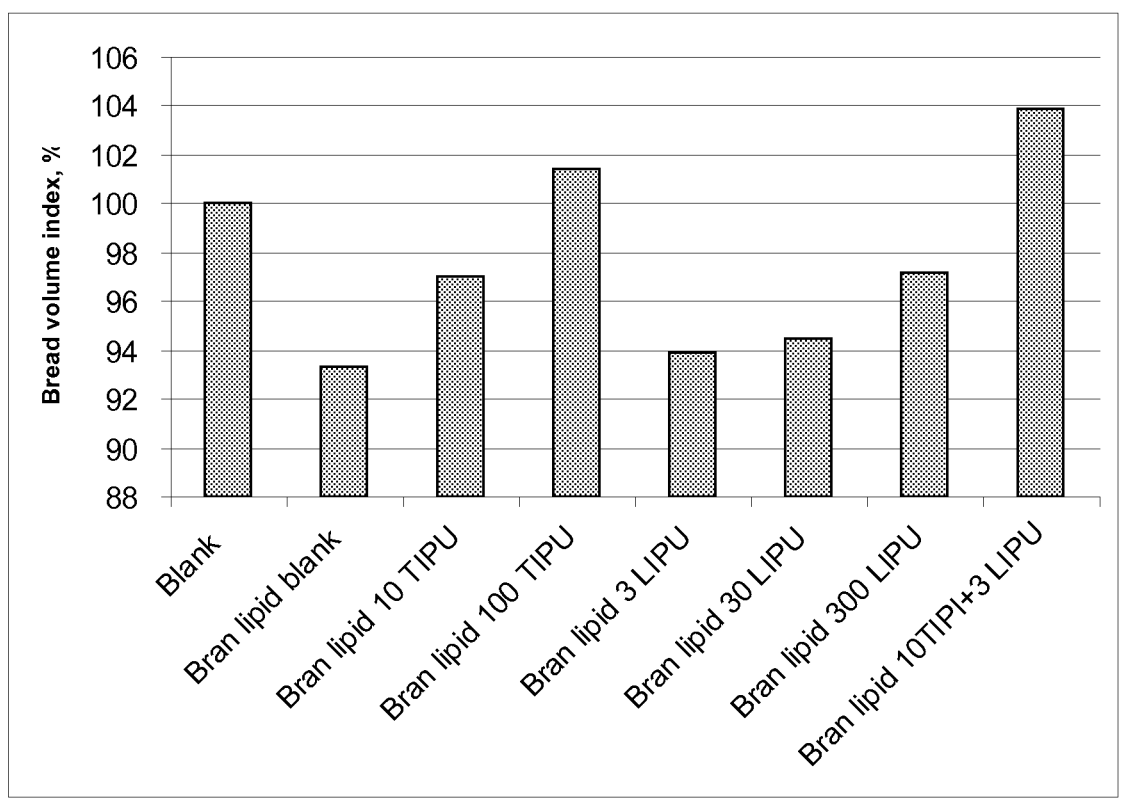

FIG. 3. Baking trial results. Rel vol of breads versus blank (%). The columns represent the baking trial experiments according to table 12.

Figure 4:
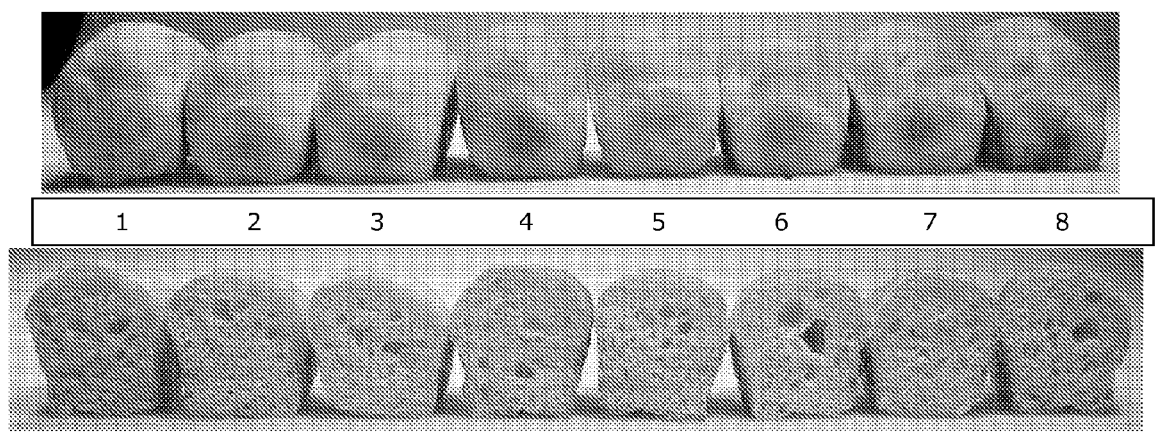

FIG. 4. Breads obtained from baking with soluble bran fractions obtained. Numbers refer to numbers in table 12.

Figure 5:
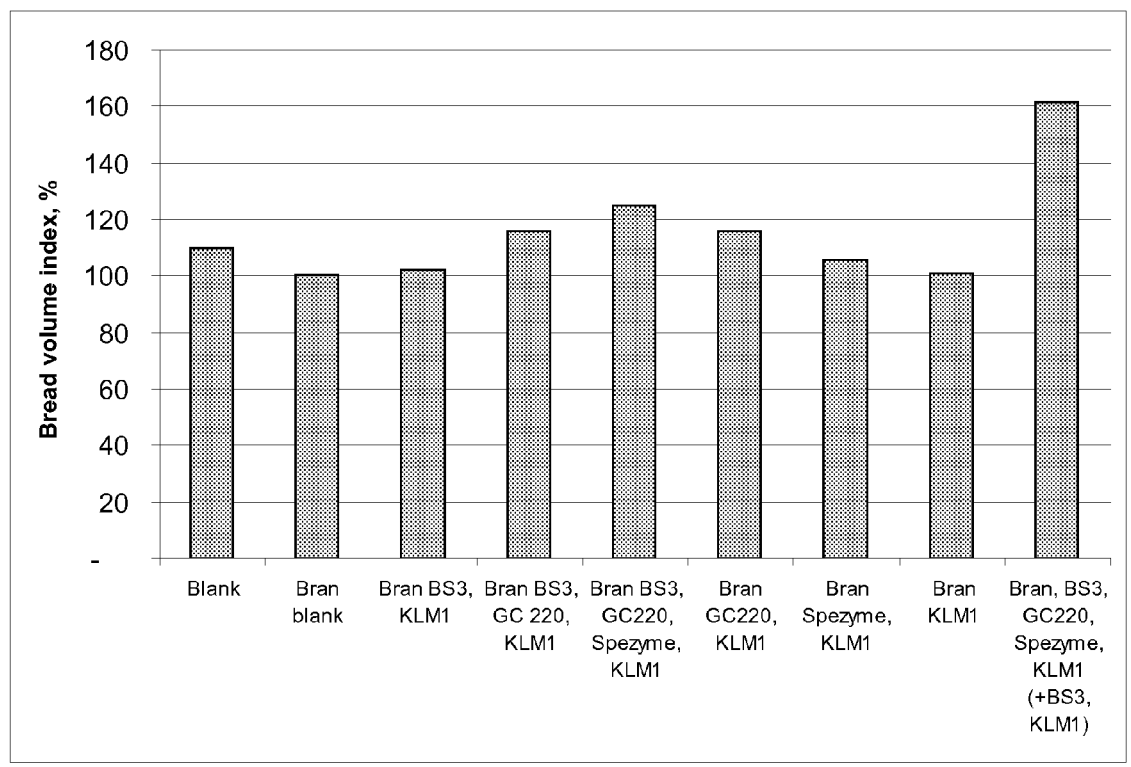

FIG. 5. Baking trial results. Rel vol of breads versus blank (%). The columns represent the baking trial experiments of according to table 17 and 18.

Figure 6:
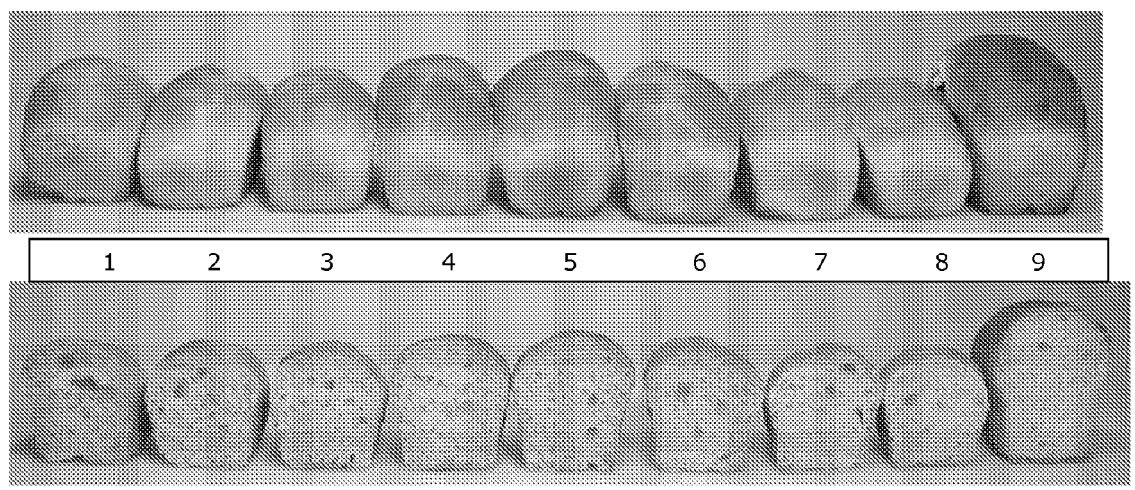

FIG. 6. Breads obtained from baking with soluble bran fractions obtained. Numbers refer to numbers in table 18.

Figure 7:

FIG. 7. Breads obtained from baking with modified bran fractions. Numbers refers to numbers in table 24.

Figure 8:
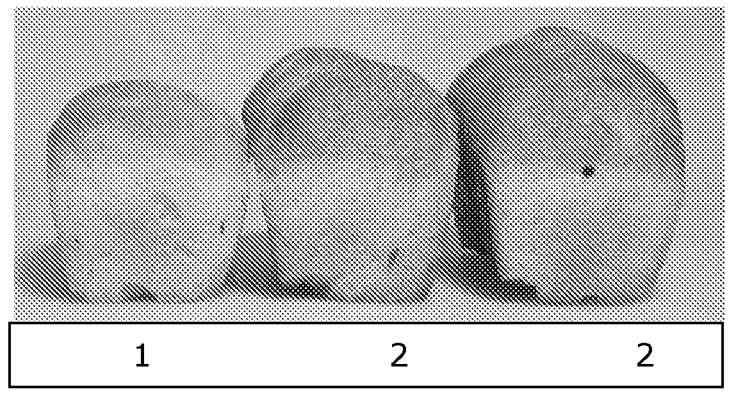

FIG. 8. Breads obtained from baking with modified rice bran extracts. Numbers refer to numbers in table 30.

Figure 9:
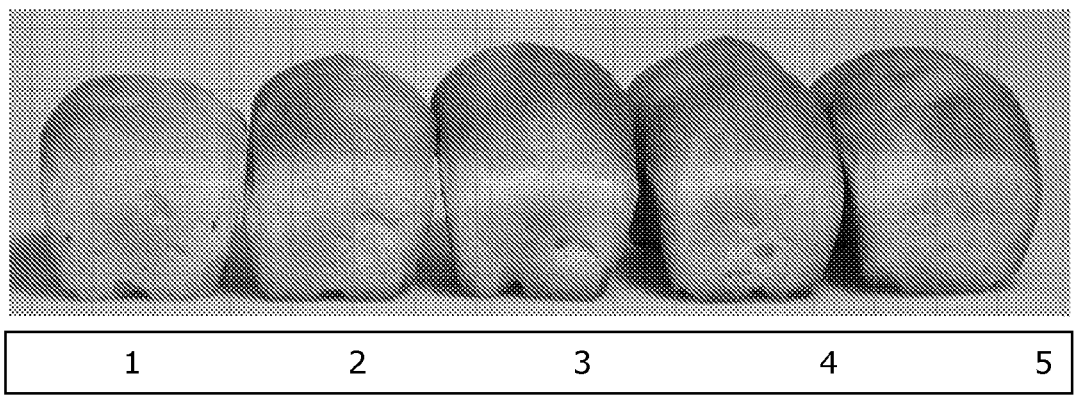

FIG. 9. Breads obtained from baking with modified bran fractions obtained. Numbers refer to numbers in table 36.

DETAILED DISCLOSURE OF THE INVENTION

Huge amounts of sidestream from processing of plant materials, such as cereal bran from milling, soap stocks from refining of vegetable oils, Distillers dried spent grain with solubles (DDGS), etc, are available as a raw material to generate functional lipids that might serve as emulsifiers in different applications like food applications, feed applications, softners in production of blast materials etc.

We here show that the modification of the lipid fraction in e.g. wheat bran is significantly increased if the material is co-treated with other enzymes like cell wall modifying enzymes and in some embodiments also starch modifying enzymes. By combining these classes of enzymes, we have seen a functionalisation of the lipids which can not be obtained using the lipases alone.

The modified lipids generated can be used in e.g. breadmaking, by adding the isolated soluble fraction or by adding the complete composition of enzyme treated bran containing the modified lipids having emulsifer properties.

Thus, the compositions genereated by the methods according to the present invention may be used as isolated solubles. However, the compositions may also be used as a mix of solubles and insolubles, i.e. in-soluble plant material, such as residual bran material. It is to be understood that part of the lipid fraction may still will be present in this residual insoluble fraction.

The term "lipid-containing plant material" as used herein refers to any material that comprises significant amounts of material derived from a plant that contain endogenous amounts of lipids. Suitably the plant material may be obtained in high amounts, contain significant amount of lipids and may be used in industrial processes.

In some embodiments the lipid-containing plant material is a side-stream, or by-products of industrial processes. In some embodiments the plant material may also contain non-plant material such as a by-product from a fermentation, that may contain yeast cells.

In some particular embodiments the lipid-containing plant material is a cereal bran, such as e.g. wheat bran from traditional milling.

In some embodiments an amount of at least about 100 mg, such as at least about 200 mg, such as at least about 300 mg per 100 dry weight of the lipid containing material is phospholipid.

In some embodiments an amount of at least about 10 mg, such as at least about 20 mg, such as at least about 30 mg per 100 g dry weight of the lipid-containing plant material is phosphatidylinositol (PI).

The phrase "partly solubilised lipid-containing plant material" as used herein refers to plant material, which contain lipids and which have been solubilised at least partly by enzymatic or mechanical action.

The term, "cereal" as used herein refers to the fruits from a plant of the family Poaceae, such seed containing at least the bran comprising the aleurone, and the starchy endosperm, with or without the additional presence of pericarp, seed coat (alternatively called testa) and/or germ. The term including but not limited to species such as wheat, barley, oat, spelt, rye, sorghum, maize, and rice.

The terms "bran" as used herein refers to a cereal-derived milling fraction enriched in any or all of the tissues to be selected from aleurone, pericarp and seed coat, as compared to the corresponding intact seed.

The term "solubilisation" as used herein refers to the solubilisation of plant material, such as cereal bran in the methods according to the invention and is intended to include any degree of solubilisation. Accordingly the "solubilisation" may be to obtain 100% soluble material or it may be to obtain a solubilisation degree less than 100%, such as less than 70%, such as in the range of 30%-60%. In some embodiments the solubilisation degree is determined on drymatter versus drymatter bran.

The term "at least partly solubilised", as used herein refers to a solubilisation degree that is higher than 1%, such as higher than 5, such as higher than 10%.

It is to be understood that the action of lipid modifying enzymes may not work optimally according to the invention, if the plant material is not solubilised to a certain extend. In the specific aspects according to the present invention, wherein the lipid modifying enzymes is added to work simultaneously with the treatment to obtain solubilisation, such as with a treatment with one or more cell-wall modifying enzyme, the solubilisation and action of lipid modifying enzymes will take place at the same time.

The term "milling fraction", as used herein, refers to all or part of the fractions resulting from mechanical reduction of the size of grains, through, as examples but not limited to, cutting, rolling, crushing, breakage or milling, with or without fractionation, through, as examples but not limited to, sieving, screening, sifting, blowing, aspirating, centrifugal sifting, windsifting, electrostatic separation, or electric field separation.

In the context of the present invention, "functional lipids", refers to lipids that have an effect on the product, wherein the functional lipid is used. In some particular embodiments, the functional lipids are emulsifiers or other food improvers.

In the context of the present invention, "cell-wall modifying enzyme", refers to any enzyme capable of hydrolysing or modifying the complex matrix polysaccharides of the plant cell wall, such as any enzyme that will have activity in the "cell wall solubilisation assay" included herein. Included within this definition of "cell-wall modifying enzyme" are cellulases, such as cellobiohydrolase I and cellobiohydrolase II, endo-glucanases and beta-glucosidases, and hemicellulolytic enzymes, such as xylanases.

The terms "cellulases" or "cellulolytic enzymes" as used herein are understood as comprising the cellobiohydrolases (EC 3.2.1.91), e.g., cellobiohydrolase I and cellobiohydrolase II, as well as the endo-glucanases (EC 3.2.1.4) and beta-glucosidases (EC 3.2.1.21).

Included with the definition of cellulases are: endoglucanases (EC 3.2.1.4) that cut the cellulose chains at random; cellobiohydrolases (EC 3.2.1.91) which cleave cellobiosyl units from the cellulose chain ends and beta-glucosidases (EC 3.2.1.21) that convert cellobiose and soluble cellodextrins into glucose. Among these three categories of enzymes involved in the biodegradation of cellulose, cellobiohydrolases are the key enzymes for the degradation of native crystalline cellulose. The term "cellobiohydrolase I" is defined herein as a cellulose 1,4-beta-cellobiosidase (also referred to as exo-glucanase, exo-cellobiohydrolase or 1,4-beta-cellobiohydrolase) activity, as defined in the enzyme class EC 3.2.1.91, which catalyzes the hydrolysis of 1,4-beta-D-glucosidic linkages in cellulose and cellotetraose, by the release of cellobiose from the non-reducing ends of the chains. The definition of the term "cellobiohydrolase II activity" is identical, except that cellobiohydrolase II attacks from the reducing ends of the chains.

The cellulases may comprise a carbohydrate-binding module (CBM) which enhances the binding of the enzyme to a cellulose-containing fiber and increases the efficacy of the catalytic active part of the enzyme. A CBM is defined as contiguous amino acid sequence within a carbohydrate-active enzyme with a discreet fold having carbohydrate-binding activity. For further information of CBMs see the CAZy internet server (Supra) or Tomme et al. (1995) in Enzymatic Degradation of Insoluble Polysaccharides (Saddler and Penner, eds.), Cellulose-binding domains: classification and properties, pp. 142-163, American Chemical Society, Washington. In a preferred embodiment the cellulases or cellulolytic enzymes may be a cellulolytic preparation as defined in U.S. application No. 60/941,251, which is hereby incorporated by reference. In a preferred embodiment the cellulolytic preparation comprising a polypeptide having cellulolytic enhancing activity (GH61A), preferably the one disclosed in WO2005/074656. The cell-wall modifying enzyme may further be a beta-glucosidase, such as a beta-glucosidase derived from a strain of the genus *Trichoderma, Aspergillus* or *Penicillium*, including the fusion protein having beta-glucosidase activity disclosed in U.S. application No. 60/832,511 (Novozymes). In some embodiments the cell-wall modifying enzyme is a CBH II, such as *Thielavia terrestris* cellobiohydrolase II (CEL6A). In some embodiments the cell-wall modifying enzyme is a cellulase enzyme, such as one derived from *Trichoderma reesei*.

The cellulolytic activity may, in some embodiments, be derived from a fungal source, such as a strain of the genus *Trichoderma*, such as a strain of *Trichoderma reesei*; or a strain of the genus *Humicola*, such as a strain of *Humicola insolens*.

In some embodiments the cell-wall modifying enzyme is a polypeptide having cellulolytic enhancing activity (GH61A) disclosed in WO 2005/074656; a cellobiohydrolase, such as *Thielavia terrestris* cellobiohydrolase II (CEL6A), a beta-glucosidase (e.g., the fusion protein disclosed in U.S. application No. 60/832,511) and cellulolytic enzymes, e.g., derived from *Trichoderma reesei*.

In some embodiments the cell-wall modifying enzyme is a polypeptide having cellulolytic enhancing activity (GH61A) disclosed in WO 2005/074656; a beta-glucosidase (e.g., the fusion protein disclosed in U.S. application No. 60/832,511) and cellulolytic enzymes, e.g., derived from *Trichoderma reesei*. In some embodiments the cell-wall modifying enzyme is a commercially available product, such as GC220 available from Genencor, A Danisco Division, US or CELLUCLAST® 1.5 L or CELLUZYME™ available from Novozymes A/S, Denmark.

Endoglucanases (EC No. 3.2.1.4) catalyses endo hydrolysis of 1,4-beta-D-glycosidic linkages in cellulose, cellulose derivatives (such as carboxy methyl cellulose and hydroxy ethyl cellulose), lichenin, beta-1,4 bonds in mixed beta-1,3 glucans such as cereal beta-D-glucans or xyloglucans and other plant material containing cellulosic parts. The authorized name is endo-1,4-beta-D-glucan 4-glucano hydrolase, but the abbreviated term endoglucanase is used in the present specification. Endoglucanase activity may be determined using carboxymethyl cellulose (CMC) hydrolysis according to the procedure of Ghose, 1987, Pure and Appl. Chem. 59: 257-268.

In some embodiments endoglucanases may be derived from a strain of the genus *Trichoderma*, such as a strain of *Trichoderma reesei*; a strain of the genus *Humicola*, such as a strain of *Humicola insolens*; or a strain of *Chrysosporium*, preferably a strain of *Chrysosporium lucknowense*.

The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain.

Examples of cellobiohydroloses are mentioned above including CBH I and CBH II from *Trichoderma reseei*; *Humicola insolens* and CBH II from *Thielavia tenrestris* cellobiohydrolase (CELL6A).

Cellobiohydrolase activity may be determined according to the procedures described by Lever et al., 1972, Anal. Biochem. 47: 273-279 and by van Tilbeurgh et al., 1982, FEBS Letters 149: 152-156; van Tilbeurgh and Claeyssens, 1985, FEBS Letters 187: 283-288. The Lever et al. method is suitable for assessing hydrolysis of cellulose in corn stover and the method of van Tilbeurgh et al., is suitable for determining the cellobiohydrolase activity on a fluorescent disaccharide derivative.

The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, J. Basic Microbiol. 42: 55-66, except different conditions were employed as described herein. One unit of beta-glucosidase activity is defined as 1.0 μmole of p-nitrophenol produced per minute at 500 C, pH 5 from 4 mM p-nitrophenyl-beta-D-glucopyranoside as substrate in 100 mM sodium citrate, 0.01% TWEEN® 20.

In some embodiments the beta-glucosidase is of fungal origin, such as a strain of the genus *Trichoderma, Aspergillus* or *Penicillium*. In some embodiments the beta-glucosidase is a derived from *Trichoderma reesei*, such as the beta-glucosidase encoded by the bgll gene (see EP 562003). In another embodiment the beta-glucosidase is derived from *Aspergillus oryzae* (recombinantly produced in *Aspergillus oryzae* according to WO 02/095014), *Aspergillus fumigatus* (recombinantly produced in *Aspergillus oryzae* according to Example 22 of WO 02/095014) or *Aspergillus niger* (1981, J. Appl. 3: 157-163).

The terms "hemicellulolvtic enzymes" or "hemicellulases", as used herein, refers to enzymes that may break down hemicellulose.

Any hemicellulase suitable for use in hydrolyzing hemicellulose, preferably into arabinoxylan oligosaccharides, may be used. Preferred hemicellulases include xylanases, arabinofuranosidases, acetyl xylan esterase, feruloyl esterase, glucuronidases, galactanase, endo-galactanase, mannases, endo or exo arabinases, exo-galactanses, pectinase, xyloglucanase, or mixtures of two or more thereof. An example of hemicellulase suitable for use in the present invention includes Grindamyl Powerbake 930 (available from Danisco A/S, Denmark) or VISCOZYM E™ (available from Novozymes A/S, Denmark). In an embodiment the hemicellulase is a xylanase. In an embodiment the xylanase is of microbial origin, such as of fungal origin (e.g., *Trichoderma, Meripilus, Humicola, Aspergillus, Fusarium*) or from a bacterium (e.g., *Bacillus*). In some embodiments the xylanase is derived from a filamentous fungus, preferably derived from a strain of *Aspergillus*, such as *Aspergillus aculeatus*; or a strain of *Humicola*, preferably *Humicola lanuginosa*. The xylanase may preferably be an endo-1,4-beta-xylanase, more preferably an endo-1,4-beta-xylanase of GH 10 or GH11. Examples of commercial xylanases include Grindamyl H121 or Grindamyl Powerbake 930 from Danisco A/S, Denmark or SHEARZYME™ and BIOFEED WHEAT™ from Novozymes A/S, Denmark.

Arabinofuranosidase (EC 3.2.1.55) catalyzes the hydrolysis of terminal non-reducing alpha-L-arabinofuranoside residues in alpha-L-arabinosides. Galactanase (EC 3.2.1.89), arabinogalactan endo-1,4-beta-galactosidase, catalyses the endohydrolysis of 1,4-D-galactosidic linkages in arabinogalactans.

Pectinase (EC 3.2.1.15) catalyzes the hydrolysis of 1,4-alpha-D-galactosiduronic linkages in pectate and other galacturonans.

Xyloglucanase catalyzes the hydrolysis of xyloglucan.

The term "xylanase" as used herein refers to an enzyme that is able to hydrolyze the beta-1,4 glycosyl bond in non-terminal beta-D-xylopyranosyl-1,4-beta-D-xylopyranosyl units of xylan or arabinoxylan. Other names include 1,4-beta-D-xylan xylanohydrolase, 1,4-beta-xylan xylanohydrolase, beta-1,4-xylan xylanohydrolase, (1-4)-beta-xylan 4-xylanohydrolase, endo-1,4-beta-xylanase, endo-(1-4)-beta-xylanase, endo-beta-1,4-xylanase, endo-1,4-beta-D-xylanase, endo-1,4-xylanase, xylanase, beta-1,4-xylanase, beta-xylanase, beta-D-xylanase. Xylanases can be derived from a variety of organisms, including plant, fungal (e.g. species of *Aspergillus, Penicillium, Disporotrichum, Neurospora, Fusarium, Humicola, Trichoderma*) or bacterial species (e.g. species of *Bacillus, Aeromonas, Streptomyces, Nocardiopsis, Thermomyces*) (see for example WO92/17573, WO92/01793, WO91/19782, WO94/21785).

In one aspect of the invention, the xylanase used in the methods of the invention is an enzyme classified as EC 3.2.1.8. The official name is endo-1,4-beta-xylanase. The systematic name is 1,4-beta-D-xylan xylanohydrolase. Other names may be used, such as endo-(1-4)-beta-xylanase; (1-4)-beta-xylan 4-xylanohydrolase; endo-1,4-xylanase; xylanase; beta-1,4-xylanase; endo-1,4-xylanase; endo-beta-1,4-xylanase; endo-1,4-beta-D-xylanase; 1,4-beta-xylan xylanohydrolase; beta-xylanase; beta-1,4-xylan xylanohydrolase; endo-1,4-beta-xylanase; beta-D-xylanase. The reaction catalyzed is the endohydrolysis of 1,4-beta-D-xylosidic linkages in xylans.

In one aspect of the invention, the xylanase of the invention is a xylanase of Glycoside Hydrolyase (GH) Family 11. The term "of Glycoside Hydrolyase (GH) Family 11" means that the xylanase in question is or can be classified in the GH family 11.

In one aspect of the invention, the xylanase used according to the invention, is a xylanase having xylanase activity as measured in the "Xylanase assay" as described herein.

According to the Cazy(ModO) site, Family 11 glycoside hydrolases can be characterised as follows:
Known Activities: xylanase (EC 3.2.1.8)
Mechanism: Retaining
Catalytic Nucleophile/Base: Glu (experimental)
Catalytic Proton Donor: Glu (experimental)
3 D Structure Status: Fold: β-jelly roll
Clan: GH-C As used herein, "Clan C" refers to groupings of families which share a common three-dimensional fold and identical catalytic machinery (see, for example, Henrissat, B. and Bairoch, A., (1996) Biochem. J., 316, 695-696).

As used herein, "Family 11" refers to a family of enzymes as established by Henrissat and Bairoch (1993) Biochem J., 293, 781-788 (see, also, Henrissat and Davies (1997) Current Opinion in Structural Biol. 1997, &:637-644). Common features for family 11 members include high genetic homology, a size of about 20 kDa and a double displacement catalytic mechanism (see Tenkanen et al., 1992; Wakarchuk et al., 1994). The structure of the family 11 xylanases includes two large β-sheets made of β-strands and α-helices.

Family 11 xylanases include the following: *Aspergillus niger* XynA, *Aspergillus kawachii* XynC, *Aspergillus tubigensis* XynA, *Bacillus circulans* XynA, *Bacilluspunzilus* XynA, *Bacillus subtilis* XynA, *Neocalliniastix patriciarum* XynA, *Streptomyces lividans* XynB, *Streptomyces lividans* XynC, *Streptomyces therinoviolaceus* XynII, *Thermomonospora fusca* XynA, *Trichoderma harzianum* Xyn, *Trichoderma reesei* XynI, *Trichoderma reesei* XynII, *Trichoderma-viride* Xyn.

In the context of the present invention, "starch modifying enzyme", refers to any enzyme that catalyze the hydrolysis of α-1,3 and/or α-1,6 glucosidic linkages in glucosides. Included within this term is glycoside hydrolases typically named after the substrate that they act upon. In some embodiments according to the invention, the "starch modifying enzyme" is selected from lactase, amylase, pullulanase, isoamylase, chitinase, sucrase, maltase, neuraminidase, invertase, hyaluronidase and lysozyme.

In some embodiments the starch modifying enzyme is a starch debranching enzyme.

In one aspect of the invention, the starch modifying enzyme used according to the invention, is an enzyme having starch debranching activity as measured in the "Starch debranching activity assay" as described herein.

Starch debranching enzymes include pullulanase (EC 3.2.1.41) and Isoamylase (EC 3.2.1.68). They hydrolyse α-1, 6-D-glucosidic branch linkages in amylopectin, β-limit dextrins and pullulans. Isomylases can be distinguished from pullulanases (EC 3.2.1.41) by the inability of isoamylase to attack pullulan, and by the limited action on α-limit dextrins.

By "amylase" is meant to include any amylase such as glucoamylases, α-amylase, β-amylases and wild-type α-amylases of Bacillus sp., such as B. licheniformis and B. subtilis. "Amylase" shall mean an enzyme that is, among other things, capable of catalyzing the degradation of starch. Amylases are hydrolases that cleave the α-D-(I→4) β-glycosidic linkages in starch. Generally, α-amylases (EC 3.2.1.1; (X-D-(I→4)-glucan glucanohydrolase) are defined as endo-acting enzymes cleaving α-D-(I→4) β-glycosidic linkages within the starch molecule in a random fashion. In contrast, the exo-acting amylolytic enzymes, such as β-amylases (EC 3.2.1.2; α-D-(I→4)-glucan maltohydrolase) and some product-specific amylases like maltogenic α-amylase (EC 3.2.1.133) cleave the starch molecule from the non-reducing end of the substrate, 13-Amylases, α-glucosidases (EC 3.2.1.20; α-D-glucoside glucohydrolase), glucoamylase (EC 3.2.1.3; α-D-(I→4)-glucan glucohydrolase), and product-specific amylases can produce glucose from starch.

By "α-amylase variant", "α-amylase variant polypeptide", and "variant enzyme" are meant an α-amylase protein that has been modified by substituting amino acid residues at the amino terminus of the mature α-amylase protein. As used herein, "parent enzymes," "parent sequence", "parent polypeptide", "wild-type α-amylase protein", and "parent polypeptides" shall mean enzymes and polypeptides from which the α-amylase variant polypeptides are derived. The parent enzyme may be a wild-type enzyme or an α-amylase that had previously been recombinantly engineered. The α-amylase variant can further include mutations in the signal sequence of the α-amylase parent polypeptide, or elsewhere in the α-amylase parent polypeptide. Thus, the α-amylase polypeptide can be a recombinantly engineered enzyme.

In one aspect of the invention, the α-amylase used according to the invention, is an α-amylase having α-amylase activity as measured in the "α-amylase assay" as described herein.

In one aspect of the invention, the beta-amylase used according to the invention, is a beta-amylase having beta-amylase activity as measured in the "beta-amylase assay" as described herein.

The term "pullulanase" refers to a specific kind of glucanase, an amylolytic endoenzyme that degrades pullulan. It is produced as, for example, an extracellular, cell surface-anchored lipoprotein by Gram-negative bacteria of the genus Klebsiella. Gram-positive bacteria, however, produce pullulanases as secreted proteins. Type I pullulanases specifically attack α-1,6 linkages, while type II pullulanases are also able to hydrolyse α-1,4 linkages. It is also produced by some other bacteria and archaea. Pullulanase is used as a detergent in biotechnology. Pullulanase (EC 3.2.1.41) is also known as pullulan-6-glucanohydrolase (debranching enzyme). Pullulan is regarded as a chain of maltotriose units linked by α-1,6-glucosidic bonds. Pullulanase will hydrolytically cleave pullulan (α-glucan polysaccharides).

The term "transglucosylation enzyme" refers to any enzyme having transglucosidase activity, such as transglucosidase. The term "transglucosidase" refers to an enzyme that transfers an α-D-glucosyl residue in a 1,4-α-D-glucan to the primary hydroxy group of glucose, free or combined in a 1,4-α-D-glucan. The transglucosidase described herein has an activity described as EC 2.4.1.24, according to IUBMB enzyme nomenclature. The systematic name for the transglucosidase described herein is 1,4-α-D-glucan:1,4-α-D-glucan (D-glucose) 6-α-D-glucosyltransferase. This enzyme may be referred to as α-glucosidase in certain publications.

As noted above, the transglucosidase enzyme generally has an activity defined as EC 2.4.1.24, according to IUBMB enzyme nomenclature, which activity transfers glucosyl residues in certain glucans to the primary hydroxy group of glucose. In some embodiments, the enzyme may also have an activity that degrades natural gum polysaccharide (e.g., xanthan, and galactomannan-containing polysaccharides such as guar gum or lima bean gum), by clipping off sugar side chains or cleaving internal bonds to break the polysaccharide backbone. Any suitable transglucosidase enzyme finds use in the present invention (See e.g., Pazur et al, Carbohydr. Res. 1986 149:137-47; and Nakamura et al, J. Biotechnol., 53:75-84, 1997). In some embodiments, the transglucosidase enzyme that find use in the present invention are commercially available (e.g., including but not limited to enzymes obtained from Megazyme, Wicklow, Ireland; or Danisco US Inc., Genencor Division, Palo Alto, Calif.). In some embodiments, the enzyme is an Aspergillus niger transglucosidase produced in Trichoderma reesei cells. In some additional embodiments, the transglucosidase is a wild type fungal transglucosidase (e.g., including but not limited to a fungal transglucosidase having an amino acid sequence deposited in NCBI's GENBANK® database as accession numbers: D45356 (GID: 2645159; Aspergillus niger), BAD06006.1 (GID:4031328; Aspergillus awamori), BAA08125.1 {GIO:\054565; Aspergillus oryzae), XPJ)OI 210809.1 (GID: 1 15492363; Aspergillus terreus), XP_001271891.1 (GID: 121707620; Aspergillus clavatus), XPJ)01266999.1 (GID: 1 19500484; Neosartorya fischeri), XP 75181 1.1 (GID:70993928; Aspergillus fumigatus), XP_659621.1 (GID:67523121; Aspergillus nidulans), XP_001216899.1 (GID: 115433524; Aspergillus terreus) and XPJ)01258585.1 (GID: 119473371; Neosartorya fischeri)), or a variant thereof that has an amino acid sequence that is at least about 70% identical, at least about 80% identical, at least about 85% identical, at least about 90% identical, at least about 95% identical, or at least about 98% identical to a wild type fungal transglucosidase.

In one aspect of the invention, the transglucosidase used according to the invention, is a transglucosidase having transglucosidase activity as measured in the "transglucosidase assay" as described herein.

Enzyme activity assays according to the invention:
Cell Wall Solubilisation Assay:
Preferably, bran solubility is measured using the following assay.

A suspension of wheat bran in (0.1 M)-di-sodium-hydrogen phosphate (0.2 M) buffer, pH 5.0 is prepared to an concentration of 1,33% bran (w/w). From this suspension, aliquots of 750 µl are transferred into eppendorph tubes under stirring. Each substrate tube is pre-heated for 5 minutes at 40° C. Hereto, 250 µl enzyme solution is added, making the end concentration of substrate 1%. Three dilutions (in duplicate) are made from each enzyme composition according to the invention, with increasing enzyme concentration (e.g. 0.33; 1.0 and 3.0 µg enzyme/gram bran) to each time of determination (0, 30, 60 and 240 minutes). As blank, a heat denaturated solution of the enzyme composition is used. The reaction is terminated to the given times, by transferring the tubes to a incubator set at 95° C. Heat denaturated samples are kept at 4° C. until all enzyme reactions are terminated. When all enzyme reactions are terminated, Eppendorph tubes are centrifuged to obtain a clear supernatant. The enzymes capability to solubilise bran is expressed as the increase in reducing end groups as determined using PAHBAH (Lever, 1972).

If the bran used contain residual starch, side activities such as amylase activity, may interfere with the above assay, bran solubilisation assay should only be carried out on purified cell wall modifying enzymes (having no amylase activity).

Alternatively the degree of solubilisation solubilisation may be measured according to the following method:

The degree of solubilisation of a plant material, e.g. cereal bran, can be determined by suspending the insoluble plant material in an extraction buffer (typically 10-25% bran in buffer (w/w)) with and without enzymes, incubate the suspension under stirring and 40 dg C for a controlled time (e.g. 30 to 1440 minuttes). After solubilisation, the solubilised material is separated from the insoluble material by centrifugation (20 min, 25000×g, room temp). The drymatter content in the supernatant is determined either by lyophilizing part of the sample, or by a moisture analysis (Moisture analyser, AND ML-50, Buch & Holm, Denmark). All the extraction buffer can not be recovered using this protocol, however, it is assumed that the concentraion of soluble material is the same in the recovered extraction buffer as in the not recovered extraction buffer, why a correction is made for the extraction buffer used in total. Having determined the drymatter content in the soluble fraction, knowing the amount of plant material taking into work and the amount of extraction buffer, the solubilisation degree can be determined using the following equation.

Solubilisation degree=(((gram drymatter/ml supernatant recovered)×(ml extraction buffer used))× 100%)/gram plant material taken into work Xylanase Assay (Endo-β-1,4-Xylanase Activity)

Samples were diluted in citric acid (0.1 M)-di-sodiumhydrogen phosphate (0.2 M) buffer, pH 5.0, to obtain approx. $OD_{590}$=0.7 in this assay. Three different dilutions of the sample were pre-incubated for 5 minutes at 40° C. At time=5 minutes, 1 Xylazyme tablet (crosslinked, dyed xylan substrate, Megazyme, Bray, Ireland) was added to the enzyme solution in a reaction volume of 1 ml. At time=15 minutes the reaction was terminated by adding 10 ml of 2% TRIS/NaOH, pH 12. Blanks were prepared using 1000 µl buffer instead of enzyme solution. The reaction mixture was centrifuged (1500×g, 10 minutes, 20° C.) and the OD of the supernatant was measured at 590 nm. One xylanase unit (XU) is defined as the xylanase activity increasing $OD_{590}$ with 0.025 per minute.

α-Amylase Activity:

α-amylases hydrolyze α-D-1,4-glucosidic linkages and its activity can be detected as a rate of color change of a starch-iodine solution due to hydrolysis of alpha 1,4-D-linkages.

Beta-Amylase Activity:

Beta-amylase activity can be detected as the liberation of maltose from the non-reducing end of a starch solution.

Transglucosidase Activity:

Transglucosidase catalyzes both hydrolytic and transfer reactions on incubation with α-D-glucooligosaccharides. Transglucosidse activity can be detected as the formation of isomaltooligosaccharides such as isomaltose, pansose and isomaltotriose upon incubation with maltose or maltodextrin.

Starch Debranching Activity Assay:

Enzymes specific for the α-D-1,6 glucosidic linkages in starch currently include isoamylase (EC 3.2.1.68) and pullulanases (EC 3.2.1.41). Enzymes acting on α-D-1,6 glucosidic linkages of starch are also classified by their action on pullulan and their activity is measured as the specific hydrolysis of α-D-1,6 glucosidic linkages of starch and pullulan.

The term "lipid modifying enzyme", as used herein refers to any enzyme that can modify a lipid.

In some preferred embodiments the lipid modifying enzyme is a lipolytic enzyme, such as a lipase.

The term "Lipolytic enzyme" as used herein refers to any enzyme that hydrolyse one or more of the fatty acids from lipids present in a plant material, such as in cereal bi-streams which can result in the formation of functional lipids within the cereal bi-stream which provide commercially value. The molecules which contribute the most significant functional effects are the molecules with emulsifier characteristics which are the partial hydrolysis products, such as lyso-phospholipids, lyso-glycolipids, and mono-glyceride molecules. The polar lipid hydrolysis products, such as lyso-phospholipids and lyso-glycolipids are particularly advantageous. In bread making, and can give equivalent functionality as emulsifiers, such as DATEM.

The substrates for lipases in the cereal bi-streams are the bran lipids which are a complex mixture of polar and non-polar lipids. The polar lipids can be divided into glycolipids and phospholipids. These lipids are built up of glycerol esterified with two fatty acids and a polar group. The polar group contributes to surface activity of these lipids. Enzymatic cleavage of one of the fatty acids in these lipids leads to lipids with a much higher surface activity. It is well known that emulsifiers, such as DATEM, with high surface activity are very functional when added to foodstuff.

The use of lipases (E.C. 3.1.1.X) in dough products may have a detrimental impact on yeast activity, and/or a negative effect on bread volume. The negative effect on bread volume is often explained by overdosing. Overdosing can lead to a decrease in gluten elasticity which results in a dough which is too stiff and thus results in reduced bread volumes. In addition, or alternatively, such lipases can degrade shortening, oil or milk fat added to the dough, resulting in off-flavour in the dough and baked product. Overdosing and off flavour have been attributed to the accumulation of free fatty acids in the dough. In relation to the present invention these un-wanted effects can be avoided as the lipase is added to the cereal bi-stream as eg. a cereal bran suspension, the functional lipids are then generated in the cereal bran suspension, which is used with or without further processing as a dough improver. A further processing can be dilution, purification of the functional lipids. Furthermore, the functional lipids may be processed to be supplied as a liquid product or as a dry formulated product, such as a freeze dried product.

In EP1193314, EP0977869, WO02/094123, WO00/32758 and also in WO01/39602, the use of lipolytic enzymes active on glycolipids was reported to be particularly beneficial in application in bread making as the partial hydrolysis products the lyso-glycolipids were found to have very high emulsifier functionality, apparently resulting in a higher proportion of positive emulsifier functionality compared to the detrimental accumulation of free fatty acids. However, the enzymes were also found to have significant non selective activity on triglyceride which resulted in unnecessarily high free fatty acid. Further the application of lipases in bread making has been the addition of lipase to the dough followed by an in-situ generation of emulsifier in the dough.

The lipase may be of any origin, e.g. of animal origin (such as, e.g. mammalian), e.g. from pancreas (e.g. bovine or porcine pancreas), or snake venom or bee venom. Alternatively, the lipase may be of microbial origin, e.g. from filamentous fungi, yeast or bacteria, such as the genus or species *Aspergillus*, e.g. *A. niger, Dictyostelium*, e.g. *D. discoideum; Magnaporthe*, e.g. *M. grisae, Mucor*, e.g. *M. javanicus, M. mucedo, M. subtilissimus; Neurospora*, e.g. *N. crassa; Rhizomucor*, e.g. *R. pusillus; Rhizopus*, e.g. *R. arrhizus, R. japonicus, R. stolonifer, Sclerotinia*, e.g. *S. libertiana; Tricho-* phyton, e.g. *T. rubrum*; *Whetzelinia*, e.g. *W. sclerotiorum*; *Bacillus*, e.g. *B. megaterium*, *B. subtilis*; *Citrobacter*, e.g. *C. freundii*; *Enterobacter*, e.g. *E. aerogenes*, *E. cloacae* *Edwardsiella*, *E. tarda*; *Erwinia*, e.g. *E. herbicola*; *Escherichia*, e.g. *E. coli*; *Klebsiella*, e.g. *K. pneumoniae*; *Proteus*, e.g. *P. vulgaris*; *Providencia*, e.g. *P. stuartii*; *Salmonella*, e.g. *S. typhimurium*; *Serratia*, e.g. *S. liquefasciens*, *S. marcescens*; *Shigella*, e.g. *S. flexneri*; *Streptomyces*, e.g. *S. violeceoruber*, *Yersinia*, e.g. *Y. enterocolitica*. Thus, the lipase may be fungal, e.g. from the class Pyrenomycetes, such as the genus *Fusarium*, such as a strain of *F. culmorum*, *F. heterosporum*, *F. solani*, or a strain of *F. oxysporum*. The phospholipase may also be from a filamentous fungus strain within the genus *Aspergillus*, such as a strain of *Aspergillus awamori*, *Aspergillus foetidus*, *Aspergillus japonicus*, *Aspergillus niger* or *Aspergillus oryzae*.

A commercially preferred source of lipolytic enzymes is a microbial lipase or acyltransferase.

In some embodiments, the lipase is from filamentous fungi, such as *Aspergillus* spp. and *Fusarium* spp. Lipases isolated from filamentous fungi have been found to have industrially applicable characteristics and also have been found to be routine to express in heterologous production systems, such as in *Aspergillus oryzae*, *Fusarium* and yeast.

In some embodiments, the lipase is from *Aspergillus tubingensis* as disclosed in EP1433852, which patent is hereby incorporated by reference.

In some embodiments, the lipase is from *Fusarium heterosporum* as disclosed in EP1722636, which patent is hereby incorporated by reference.

In some embodiments, the lipase is from *Fusarium oxysporum* as identified in EP 0 130 064, or in Hoshino et al. (1992) Biosci. Biotech. Biochem 56: 660-664.

In some embodiments, the lipase is porcine pancreatic phospholipase A2 for example expressed in *Aspergillus niger* (Cakezyme™, DSM).

In some embodiments, the lipase is as described in EPO 869 167, wherein the cloning and expression of a *Fusarium oxysporum* lipase and its use in baking is disclosed. The enzyme is described as having phospholipase activity. This enzyme is now sold by Novozymes A/S (Denmark) as Lipopan F™.

In some embodiments, the lipase is as described in WO 02/00852, which discloses five lipase enzymes and their encoding polynucleotides, isolated from *F. venenatum*, *F. sulphureum*, *A. berkeleyanum*, *F. culmorum* and *F. solani*. All five enzymes are described as having triacylglycerol hydrolysing activity, phospholipase and galactolipase activity. Three of the enzymes have equivalent activity to the *F. oxysporum* enzyme taught in EP 0 869 167: *F. venenatum*, *F. sulphureum*, *F. culmorum*.

In some embodiments, the lipid modifying enzyme is a lipolytic enzyme variant. Lipolytic enzyme variants, with specific amino acid substitutions and fusions, have been produced, some of which have an enhanced activity on the polar lipids compared to the wild-type parent enzymes. WO01/39602 describes such a variant, referred to as SP979, which is a fusion of the *Thermomyces lanuginosus* lipase, and the *Fusarium oxysporum* lipase described in EP 0 869 167. This variant has been found to have a significantly high ratio of activity on phospholipids and glycolipids compared to triglycerides.

In some embodiments, the lipid modifying enzyme is a lipid acyltransferase.

The term "lipid acyltransferase" as used herein means an enzyme which as well as having lipase activity (generally classified as E.C. 3.1.1.x in accordance with the Enzyme Nomenclature Recommendations (1992) of the Nomenclature Committee of the International Union of Biochemistry and Molecular Biology) also has acyltransferase activity (generally classified as E.C. 2.3.1.x), whereby the enzyme is capable of transferring an acyl group from a lipid to one or more acceptor substrates, such as one or more of the following: a sterol; a stanol; a carbohydrate; a protein; a protein subunit; glycerol.

In some embodiments, the lipid acyltransferase for use in the methods and/or uses of the present invention is capable of transferring an acyl group from a lipid (as defined herein) to one or more of the following acyl acceptor substrates: a sterol, a stanol, a carbohydrate, a protein or subunits thereof, or a glycerol.

For some aspects the acyl acceptor may be any compound comprising a hydroxy group (—OH), such as for example, polyvalent alcohols, including glycerol; sterol; stanols; carbohydrates; hydroxy acids including fruit acids, citric acid, tartaric acid, lactic acid and ascorbic acid; proteins or a subunit thereof, such as amino acids, protein hydrolysates and peptides (partly hydrolysed protein) for example; and mixtures and derivatives thereof.

In some embodiments, the lipid substrate upon which the lipid acyltransferase used according to the present invention acts is one or more of the following lipids: a phospholipid, such as a lecithin, e.g. phosphatidylcholine, a triacylglyceride, a cardiolipin, a diglyceride, or a glycolipid, such as digalactosyldiglyceride (DGDG) for example. The term lecithin as used herein encompasses phosphatidylcholine, phosphatidylethanolamine, phosphatidylinositol, phosphatidylserine and phosphatidylglycerol.

For some aspects, preferably the lipid substrate upon which the lipid acyltransferase acts is a phospholipid, such as lecithin, for example phosphatidylcholine or phosphatidylinositol.

In some embodiments the lipid substrate is a food lipid, that is to say a lipid component of a foodstuff.

Suitably, the lipid acyltransferase used according to the present invention may exhibit one or more of the following lipase activities: glycolipase activity (E.C. 3.1.1.26), triacylglycerol lipase activity (E.C. 3.1.1.3), phospholipase A2 activity (E.C. 3.1.1.4) or phospholipase A1 activity (E.C. 3.1.1.32). The term "glycolipase activity" as used herein encompasses "galactolipase activity".

Suitably, the lipid acyltransferase used according to the present invention may have at least one or more of the following activities: glycolipase activity (E.C. 3.1.1.26) and/or phospholipase A1 activity (E.C. 3.1.1.32) and/or phospholipase A2 activity (E.C. 3.1.1.4).

For some aspects, preferably the lipid acyltransferase used according to the present invention is capable of transferring an acyl group from a glycolipid and/or a phospholipid to a sterol and/or a stanol to form at least a sterol ester and/or a stanol ester.

Suitable sterol acyl acceptors include cholesterol and phytosterols, for example alpha-sitosterol, beta-sitosterol, stigmasterol, ergosterol, campesterol, 5,6-dihydrosterol, brassicasterol, alpha-spinasterol, beta-spinasterol, gamma-spinasterol, deltaspinasterol, fucosterol, dimosterol, ascosterol, serebisterol, episterol, anasterol, hyposterol, chondrillasterol, desmosterol, chalinosterol, poriferasterol, clionasterol, sterol glycosides, and other natural or synthetic isomeric forms and derivatives.

In one aspect, preferably the acyl acceptor is one or more of the following: alpha-sitosterol, beta-sitosterol, stigmasterol, ergosterol, beta-sitostanol, ss-sitostanol or campesterol.

For some aspects, preferably the lipid acyltransferase used according to the present invention is capable of transferring an acyl group from a glycolipid and/or a phospholipid to glycerol to form at least a diglyceride and/or a monoglyceride.

For some aspects, one or more sterols present in the lipid-containing plant material may be converted to one or more stanols prior to or at the same time as the lipid acyltransferase is added according to the present invention. Any suitable method for converting sterols to stanols may be employed. For example, the conversion may be carried out by chemical hydrogenation for example. The conversion may be conducted prior to the addition of the lipid acyltransferase in accordance with the present invention or simultaneously with the addition of the lipid acyltransferase in accordance with the present invention. Suitably enzymes for the conversion of sterol to stanols are taught in WO00/061771.

Suitably the present invention may be employed to produce phytostanol esters in the lipid plant material. Phytostanol esters have increased solubility through lipid membranes, bioavailability and enhanced health benefits (see for example WO92/99640).

Protocol for the Determination of % Acyltransferase Activity:

The lipid-containing plant material to which a lipid acyltransferase has been added according to the present invention may be extracted following the enzymatic reaction with $CHCl_3:CH_3OH$ 2:1 and the organic phase containing the lipid material is isolated and analysed by GLC and HPLC according to the procedure detailed herein below. From the GLC and HPLC analyses the amount of free fatty acids and one or more of sterol/stanol esters; carbohydrate esters, protein esters; diglycerides; or monoglycerides are determined. A control of the lipid-containing plant material to which no enzyme has been added, is analysed in the same way.

Calculation:

From the results of the GLC and HPLC analyses the increase in free fatty acids and sterol/stanol esters and/or carbohydrate esters and/or protein esters and/or diglycerides and/or monoglycerides can be calculated:

Δ% fatty acid=% Fatty acid(enzyme)−% fatty acid (control); Mv fatty acid=average molecular weight of the fatty acids;

$A$=Δ% sterol ester/Mv sterol ester(where Δ% sterol ester=% sterol/stanol ester(enzyme)−% sterol/stanol ester(control) and Mv sterol ester=average molecular weight of the sterol/stanol esters)−applicable where the acyl acceptor is a sterol and/or stanol;

$B$=Δ% carbohydrate ester/Mv carbohydrate ester (where Δ% carbohydrate ester=% carbohydrate ester(enzyme)−% carbohydrate ester(control) and Mv carbohydrate ester=average molecular weight of the carbohydrate ester)−applicable where the acyl acceptor is a carbohydrate;

$C$=Δ% protein ester/Mv protein ester(where Δ% protein ester=% protein ester(enzyme)−% protein ester(control) and Mv protein ester=average molecular weight of the protein ester)−applicable where the acyl acceptor is a protein; and $D$=absolute value of diglyceride and/or monoglyceride/Mv di/monoglyceride(where Δ% diglyceride and/or monoglyceride=% diglyceride and/or monoglyceride(enzyme)−% diglyceride and/or monoglyceride (control) and Mv di/monoglyceride=average molecular weight of the diglyceride and/or monoglyceride)−applicable where the acyl acceptor is glycerol.

The transferase activity is calculated as a percentage of the total enzymatic activity:

$$\% \text{ transferase activity} = \frac{A^* + B^* + C^* + D^* \times 100}{A^* + B^* + C^* + D^* + \Delta \% \text{ fatty acid}/(Mv \text{ fatty acid})}$$

(*- delete as appropriate).

In a preferred aspect the present invention provides a lipid-containing plant material wherein the lipids have been modified into functional lipids by the action of lipolytic enzymes. This can be used either with or without purification of the functional lipids as a foodstuff ingredient.

Suitably, the term "foodstuff" as used herein may mean a foodstuff in a form which is ready for consumption. Alternatively or in addition, however, the term foodstuff as used herein may mean one or more food materials which are used in the preparation of a foodstuff. By way of example only, the term foodstuff encompasses both baked goods produced from dough as well as the dough used in the preparation of said baked goods.

Suitably, the term "foodstuff" as used herein means a substance which is suitable for human and/or animal consumption.

In another aspect, the foodstuff in accordance with the present invention may be an animal feed.

In some embodiments, the foodstuff used according to the present invention is selected from one or more of the following: eggs, egg-based products, including but not limited to mayonnaise, salad dressings, sauces, ice creams, egg powder, modified egg yolk and products made therefrom; baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including cheese, butter, milk, coffee cream, whipped cream, custard cream, milk drinks and yoghurts; mousses, whipped vegetable creams, meat products, including processed meat products; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions and sauces.

Suitably the foodstuff in accordance with the present invention may be a "fine foods", including cakes, pastry, confectionery, chocolates, fudge and the like.

In one aspect the foodstuff in accordance with the present invention may be a dough product or a baked product, such as a bread, a fried product, a snack, cakes, pies, brownies, cookies, noodles, instant noodles, tortillas, snack items such as crackers, graham crackers, pretzels, and potato chips, and pasta, and breakfast cereals.

In a further aspect, the foodstuff in accordance with the present invention may be a plant derived food product such as flours, pre-mixes, oils, fats, cocoa butter, coffee whitener, salad dressings, margarine, spreads, peanut butter, shortenings, ice cream, cooking oils.

In another aspect, the foodstuff in accordance with the present invention may be a dairy product, including butter, milk, cream, cheese such as natural, processed, and imitation cheeses in a variety of forms (including shredded, block, slices or grated), cream cheese, ice cream, frozen desserts, yoghurt, yoghurt drinks, butter fat, anhydrous milk fat, other dairy products. The enzyme used according to the present invention may improve fat stability in dairy products.

In another aspect, the foodstuff in accordance with the present invention may be a food product containing animal derived ingredients, such as processed meat products, cooking oils, shortenings.

In a further aspect, the foodstuff in accordance with the present invention may be a beverage, a fruit, mixed fruit, a vegetable or wine. In some cases the beverage may contain up to 20 g/l of added phytosterols derived from the invention.

In another aspect, the foodstuff in accordance with the present invention may be an animal feed. The animal feed may be enriched with phytosterol and/or phytostanols, preferably with beta-sitosterol/stanol. Suitably, the animal feed may be a poultry feed. When the foodstuff is poultry feed, the present invention may be used to lower the cholesterol content of eggs produced by poultry fed on the foodstuff according to the present invention.

In one aspect preferably the foodstuff is selected from one or more of the following: eggs, egg-based products, including mayonnaise, salad dressings, sauces, ice cream, egg powder, modified egg yolk and products made therefrom.

Preferably the foodstuff according to the present invention is a water containing foodstuff. Suitably the foodstuff may be comprised of 10-98% water, suitably 14-98%, suitably of 18-98% water, suitably of 20-98%, suitably of 40-98%, suitably of 50-98%, suitably of 70-98%, suitably of 75-98%.

In one aspect of this invention the functional lipid produced from the lipid-containing plant material is an emulsifier. Preferable, at least one emulsifier is generated in the lipid-containing plant material.

In one aspect of the invention at least two different emulsifiers are generated in the lipid containing material.

In one aspect of the invention at least three different emulsifiers are generated in the lipid containing material.

In one aspect of the invention at least four emulsifiers are generated in the lipid containing material.

Suitably, the emulsifier in accordance with the present invention may be for example one or more of the following: a diglyceride, a monoglyceride, such as 1-monoglyceride or a lysolecithin, such as lysophosphatidylcholine or phosphatidylinositol, for example, a digalactosyl monoglyceride (DGMG). The emulsifier is preferably produced from the lipid acyl donor following removal of one or more acyl groups from said lipid acyl donor. The term lysolecithin as used herein encompasses lysophosphatidylcholine, lysophosphatidylethanolamine, lysophosphatidylinositol, lysophosphatidylserine and lysophosphatidylglycerol. The term lysophosphatidylcholine as used herein is synonymous with the term lysolecithin and these terms may be used herein interchangeably.

Where one of the emulsifiers is a protein ester and/or a diglyceride and/or a monoglyceride, the second emulsifier may be for example one or more of the following: a diglyceride, a monoglyceride, such as 1-monoglyceride, lysophosphatidylcholine, or digalactosyl monoglyceride (DGMG). The second emulsifier is preferably produced from the lipid acyl donor following removal of one or more acyl groups from said lipid acyl donor.

In one embodiment the generated functional lipids of the invention can be used in a process for the preparation of a foodstuff.

The functional lipids according to the present invention may be used with one or more other suitable food grade enzymes. Thus, it is within the scope of the present invention that, in addition to the functional lipids of the invention, at least one further enzyme is added to the foodstuff. Such further enzymes include starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases, glucolipases and hexose oxidase, and proteases.

The lipid-containing plant material treated with lipolytic enzymes to generate functional lipids according to the present invention may be used without purification or with limited purification of the functional lipids together with one or more other suitable food grade enzymes. Thus, it is within the scope of the present invention that, in addition to the purified or un-purified functional lipids of the invention, at least one further enzyme is added to the foodstuff. Such further enzymes include starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases, glucolipases and hexose oxidase, and proteases.

In one preferred embodiment the lipolytic enzyme has one or more of the following lipase activities: glycolipase activity (E.C. 3.1.1.26, triacylglycerol lipase activity (E.C. 3.1.1.3), phospholipase A2 activity (E.C. 3.1.1.4) or phospholipase A1 activity (E.C. 3.1.1.32). Suitably, lipase enzymes are well know within the art and include by way of example the following lipases: Grindamyl Powerbake 4070 or 4080 (Danisco A/S), Lysomax Oil (Danisco A/S), Lipopan® F, Lipopan® Xtra, and/or LECITASE® ULTRA (Novozymes A/S, Denmark), phospholipase A2 (e.g. phospholipase A2 from LIPOMOD™ 22 L from Biocatalysts, LIPOMAX™ from Genencor), LIPOLASE® (Novozymes A/S, Denmark), Panomore™ (DSM Nutritional Products), the lipases taught in WO03/97835, EP 0 977 869 or EP 1 193 314. A person skilled in the art will be able to combine proportions of lipolytic enzymes.

Traditionally the cake industry uses cake improvers for the production of cakes and to secure high quality cakes in terms of taste, structure, eating quality and appearance. These cake improvers are normally based on emulsifiers spray dried on a carrier like starch and malto dextrin. Some cake improvers are also in a gel form based on emulsifiers, sugars and water. These cake improvers are very important for the cake industry in order to produce cake of high quality. Cake improvers however contain emulsifiers and other "non-natural" ingredients with an E-number. Because of demand for the consumers to reduce the numbers of E-numbers, the cake industry has asked for alternative ways to produce cakes of high quality without using this kind of emulsifiers.

The lipid-containing plant material treated with lipolytic enzymes to generate functional lipids according to the present invention may be used as food improvers either without purification or with limited purification of the functional lipids or as completely purified functional lipids.

In one aspect of the invention the food improver is a cake improver.

In one aspect of the invention the food improver is a bread improver.

The food improver generated according to the present invention may suitably comprise one or more of the following additives:

soy protein material; carotenoids, flavenoids, antioxidant and phytochemical (especially anthocyanonide, carotenoid, bioflavinoid, glutathione, catechin, isoflavone, lycopene, ginsenoside, pycnogenol, alkaloid, pygeum phytosterol, sulphoraphone, resveretol, grape seed extract or food containing stanol esters), vitamin (especially vitamin C, vitamin A, vitamin B3, vitamin D, vitamin E, thiamine, riboflavin, niacin, pyridoxine, cyanocobalamin, folic acid, biotin, pantothenic acid or vitamin K), minerals (especially calcium, iodine, magnesium, zinc, iron, selenium, manganese, chromium, copper, cobalt, molybdenum or phosphorus), fatty acid (especially gamma-linoleic acid, ucospentaenoic acid or decosahexaenoic acid), oil (especially borage oil, high carotenoid canola oil or flax seed oil), glucerol, sorbitol, amino acid (especially tryptophan, lysine, methionine, phenylalanine, threonine, valine, leucine, isoleucine, alanine, arginine, aspartic acid, cystine, cysteine, glutamic acid, glutamine, glycine, histidine, proline, hydroxyproline, serine, taurine or tyrosine), enzyme as defined above (especially bromelain, papain, amylase, cellulase or coenzyme Q), lignin, stanol ester or friendly bacteria (especially *Lactobacillus acidophilus, Lactobacillus bulgaricus, Lactobacillus bifidus, Lactobacillus plantarum* or *Streptococcus* faecium), folic acid, insoluble and/or soluble fibre.

The present invention may provide one or more of the following unexpected technical effects in egg products, particularly mayonnaise: improved heat stability during pasteurisation; improved organoleptic properties, an improved consistency.

The present invention may provide one or more of the following unexpected technical effects in dough and/or baked products: an improved specific volume of either the dough or the baked products (for example of bread and/or of cake); an improved dough stability; an improved crust score (for example a thinner and/or crispier bread crust), an improved crumb score (for example a more homogenous crumb distribution and/or a finer crumb structure and/or a softer crumb); an improved appearance (for example a smooth surface without blisters or holes or substantially without blisters or holes); a reduced staling; an enhanced softness; an improved odour; an improved taste.

The present invention may provide a beneficial effect from the functional lipids as these functions as highly surface-active materials in a foodstuff without formation of substantial amount of free fatty acids, which reduce the ability of the foodstuff to oxidize upon storage, because free fatty acids are more prone to oxidation than the corresponding fatty acid esters.

In a further aspect the present invention provides the use of a lipolytic enzyme to generate other functional compounds according to the present invention in a lipid-containing plant material.

It is to be understood that the action of the lipid modifying enzymes, such as lipolytic enzymes on the lipid-containing plant material may not only generate functional lipids, but also other functional compounds, such as with the action of a lipid transferase, wherein an acyl group from a lipid is transferred to one or more other acceptor substrates, such as one or more of the following: a sterol; a stanol; a carbohydrate; a protein; a protein subunit; and glycerol.

In some particular embodiments the functional compounds generated in the methods according to the present invention are functional esters.

In some embodiments, both functional lipids and other functional compounds are generated by the methods according to the present invention.

These functional compounds generated by the methods according to the present invention may then be used in the manufacture of a dough and/or a baked product, comprising adding said functional compounds to a dough, and (optionally) baking the dough to make a baked product for one or more of the following: reducing stickiness of the dough; improving machinability of the dough; reducing blistering during baking of the baked product; improving bread volume and/or softness; prolonging shelf life of the baked product and/or dough; improving antistaling effect of the baked product and/or dough; improving crumb structure of the baked product; reducing pore heterogeneity of the baked product; improving pore homogeneity of the baked product; reducing mean pore size of the baked product; enhancing the gluten index of the dough; improving flavour and/or odour of the baked product, improving the colour of the crust of the baked product.

In one aspect the functional compounds generated by the methods according to the present invention are purified or partly purified.

In one aspect the functional compounds generated by the methods according to the present invention are not further purified before use in a foodstuff.

In one aspect the functional compounds generated by the methods according to the present invention are formulated into a dry product.

In one aspect the functional compounds are concentrated or diluted before use in a foodstuff.

In another aspect of the invention, there is provided a method of making noodles, or a noodle dough or a noodle-based product, which method comprises adding a functional compound according to the present invention to the noodle, noodle dough or noodle-based product.

In one aspect of the present invention, there is provided a use of a functional compound according to the present invention in the manufacture of a noodle or a noodle-based product for one or more of improving colour/yellowness, stabilising colour characteristics, reducing brightness, reducing fat content, improving texture and bite (chewiness), reducing water activity, reducing breakage, increasing core firmness and improving shape retention during processing.

In another aspect of the invention, there is provided a method of making a tortilla or tortilla dough, which method comprises adding a food improver generated according to the present invention to the tortilla or tortilla dough.

In another aspect of the invention, there is provided a method of making pasta or whole grain pasta or a pasta dough, which method comprises adding a food improver generated according to the present invention to the pasta or pasta dough.

A further aspect of the present invention provides the use of a food improver generated according to the present invention in the manufacture of a tortilla or a tortilla dough for improving the rollability of a tortilla, increasing pliability of a tortilla, improving antistaling properties of the tortilla and/or tortilla dough, improving softness and/or reducing off-flavour in the tortilla and/or tortilla dough.

The functionality of the food improver may be improved by combination with emulsifiers such as DATEM.

Suitably, the present invention may provide one or more of the following unexpected technical effects in a foodstuff: an improved appearance, an improved mouthfeel, an improved stability, in particular an improved thermal stability, an improved taste, an improved softness, an improved resilience, an improved emulsification.

Suitably, the present invention may provide one or more of the following unexpected technical effects in dairy products, such as ice cream for example: an improved mouthfeel (preferably a more creamy mouthfeel); an improved taste; an improved meltdown.

Suitably, the present invention may provide one or more of the following unexpected technical effects in egg or in egg products: improved stability of emulsion; thermal stability of emulsion; improved flavour; reduced mal-odour; improved thickening properties, improved consistency.

Specific technical effects associated with the use of the food improver as defined herein in the preparation of a foodstuff are listed in the table below:

|    | Foodstuff | Effect |
| --- | --- | --- |
| 1  | Bread, Muffins and Doughnuts | Strengthens dough and increases mechanical resistance and increases water absorption capacity. Increases volume of bakery products and maintains softness of crumb |
| 2  | Frozen dough | Prevents spoiling during refrigeration |
| 3  | Sponge cake | Makes good cake volume and a uniform soft texture |
| 4  | Biscuit, cracker and cookie | Makes stable emulsions of fat and prevents stickiness to the machine. Prevents blooming of high fat products |
| 5  | Batter and breading | Improves texture of fried products. |
| 6  | Noodles | Prevents dough from sticking to the machine. Increases water content, and decreases cooking loss |
| 7  | Instant noodles | Prevent noodles form adhering to each other |
| 8  | Pasta | Dough conditioner prevents adhesion on cooking. |
| 9  | Custard cream | Makes starch paste with a smooth and creamy texture, and prevents dehydration. |
| 10 | Coffee whitener | Prevent oil and water separation |
| 11 | Whipping cream | Provides stable emulsion |
| 12 | Chocolate | Prevents or reduced blooming |
| 13 | Caramel, candy and nougat | Improves emulsification of molten sugar and oil. Prevents separation of oil. |
| 14 | Processed meat, sausages | Improves water holding capacity of sausages and pressed ham, and prevents separation of oil phase of pastes and pâté. |

In a further aspect of the present invention provides the use of a lipolytic enzyme in a process of preparing functional lipids.

In another aspect of the present invention there is provided a process of preparing a lyso-phospholipid, for example lyso-lecithin, which process comprises treating a lipid-containing plant material with the lipolytic enzyme according to the present invention.

In a further aspect of the present invention provides the use of a lipolytic enzyme in a process of preparing a lyso-glycolipid, (for example digalactosyl monoglyceride (DGMG) or monogalactosyl monoglyceride (MGMG)) by treatment of a lipid-containing plant material with the lipolytic enzyme according to the present invention.

In some embodiments of the invention, the liquid suspension of an at least partly solubilised lipid-containing plant material is essentially free from starch.

In some embodiments of the invention, less than about 50%, such less than about 40%, such as less than about 30%, such as less than about 20%, such as less than about 10%, such as less than about 6%, such as less than about 3%, such as less than about 1% (w/w) of the liquid suspension of an at least partly solubilised lipid-containing plant material is starch or components containing starch, such as flour.

Accordingly, in some embodiments it is to be understood that the enzymes are to have an enzymatic effect on the lipid-containing plant material which is essentially free from starch or which only contain residual starch from a previous processing step. The present invention is not intended to cover the enzymatic treatment of compositions with additional added flour preparations, such as in situ enzymatic bread making applications.

Determination of Galactolipase Activity (Glycolipase Activity Assay):

Substrate:

0.6% digalactosyldiglyceride (Sigma D 4651), 0.4% Triton-X 100 (Sigma X-100) and 5 mM CaCl2 was dissolved in 0.05M HEPES buffer pH 7.

Assay Procedure:

400 µL substrate was added to an 1.5 mL Eppendorf tube and placed in an Eppendorf Thermomixer at 37° C. for 5 minutes. At time t=0 min, 50 µL enzyme solution was added. Also a blank with water instead of enzyme was analyzed. The sample was mixed at 10*100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity GLU at pH 7 was calculated as micromoles of fatty acid produced per minute under assay conditions.

Determination of Phospholipase Activity (Phospholipase Activity Assay):

Phospholipase activity was measured using two different methods which give comparable results. Either of these methods can be used to determine phospholipase activity in accordance with the present invention.

"PLU Assay" for Determination of Phospholipase Activity

Substrate:

0.6% L-α Phosphatidylcholine 95% Plant (Avanti #441601), 0.4% Triton-X 100 (Sigma X-100) and 5 mM $CaCl_2$ was dissolved in 0.05 M HEPES buffer pH 7.

Assay Procedure:

400 µL substrate was added to an 1.5 mL Eppendorf tube and placed in an Eppendorf Thermomixer at 37° C. for 5 minutes. At time t=0 min, 50 µL enzyme solution was added. Also a blank with water instead of enzyme was analyzed. The sample was mixed at 10*100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity PLU-7 at pH 7 was calculated as micromoles of fatty acid produced per minute under assay conditions "TIPU assay" for determination of phospholipase activity 1 TIPU (Titration Phospholipase Unit) is defined as the amount of enzyme, which liberates 1 µmmol free fatty acid per minute at the assay conditions.

Phospholipase A1 and A2 catalyse the conversion of lecithin to lyso-lecithin with release of the free fatty acid from position 1 and 2, respectively. Phospholipase activity can be determined by continous titration of the fatty acids liberated from lecithin during enzymation, since the consumption of alkali equals the amount of fatty acid liberated.

Substrate:

4% lecithin, 4% Triton-X 100, and 6 mM CaCl2: 12 g lecithin powder (Avanti Polar Lipids #44160) and 12 g Triton-X 100 (Merck 108643) was dispersed in approx. 200 ml demineralised water during magnetic stirring. 3.0 ml 0.6 M CaCl2 (p.a. Merck 1.02382) was added. The volume was adjusted to 300 mL with demineralised water and the emulsion was homogenised using an Ultra Thurax. The substrate was prepared freshly every day.

Assay Procedure:

An enzyme solution was prepared to give a slope on the titration curve between 0.06 and 0.18 ml/min with an addition of 300 μL enzyme.

A control sample of known activity is included.

The samples were dissolved in demineralised water and stirred for 15 min. at 300 rpm.

25.00 ml substrate was thermostatted to 37.0° C. for 10-15 minutes before pH was adjusted to 7.0 with 0.05 M NaOH. 300 μL enzyme solution was added to the substrate and the continuous titration with 0.05 M NaOH was carried out using a pH-Stat titrator (Phm 290, Mettler Toledo). Two activity determinations are made on each scaling.

After 8 minutes the titration is stopped and the slope of the titration curve is calculated between 5 and 7 minutes. The detection limit is 3 TIPU/ml enzyme solution.

Calculations:

The phospholipase activity (TIPU/g enzyme) was calculated in the following way:

$$TIPU/g = \frac{\alpha \cdot N \cdot 10^6 \frac{\mu mol}{mol} \cdot 10^{-3} \frac{1}{ml} \cdot V_1}{m \cdot V_2} = \frac{\alpha \cdot N \cdot 10^3 \cdot V_1}{m \cdot V_2}$$

Where:

α is the slope of the titration curve between 5 and 7 minutes of reaction time (ml/min).

N is the normality of the NaOH used (mol/l).

V1 is the volume in which the enzyme is dissolved (ml).

m is the amount of enzyme added to V1 (g).

V2 is the volume of enzyme solution added to the substrate (ml).

Determination of Triacylglyceride Lipase Activity: Assay Based on Triglyceride (Tributyrin) as Substrate (LIPU):

Lipase activity based on tributyrin is measured according to Food Chemical Codex, Forth Edition, National Academy Press, 1996, p 803, ith the modifications that the sample is dissolved in deionized water instead of glycine buffer, and the pH stat set point is 5.5 instead of 7.

1 LIPU is defined as the quantity of enzyme which can liberate 1 mol butyric acid per minute under assay conditions.

In one aspect of the invention, the lipolytic enzyme used according to the present invention may be obtainable from a filamentous fungus. More preferably, the fungal lipolytic enzyme is obtainable (preferably obtained) from *Fusarium* spp. Preferably, the fungal lipolytic enzyme used according to the present invention may be obtainable (preferably obtained) from *Fusarium heterosporum* or *Fusarium semitectum*. Suitably, the fungal lipolytic enzyme used according to the present invention may be obtainable (preferably obtained) from *Fusarium heterosporum* (CBS 782.83) or *Fusarium semitectum* (IBT 9507).

Thus in one aspect, preferably the lipolytic enzyme used according to the present invention is a filamentous fungal lipolytic enzyme, preferably a filamentous fungal wild-type lipolytic enzyme.

In some of the applications mentioned herein, particularly the food applications, such as the bakery applications, the food improver generated according to the present invention may be used with one or more conventional emulsifiers, including for example monoglycerides, diacetyl tartaric acid esters of mono- and diglycerides of fatty acids, sodium stearoyl lactylate (SSL) and lecithins.

The food improver generated by the methods according to the present invention is especially preferred in bread recipes with added fat.

In addition or alternatively, the food improver generated by the methods according to the present invention may be used with one or more other suitable food grade enzymes. Thus, it is within the scope of the present invention that, in addition to the lipolytic enzyme of the present invention, at least one further enzyme may be added to the baked product and/or the dough. Such further enzymes include starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases, galatolipases and hexose oxidase, proteases, and acyltransferases (such as those described in WO04/064987 for instance).

It is particularly preferred that the lipolytic enzyme used according to the present invention is used in combination with alpha amylases in producing food products. In particular, the amylase may be a non-maltogenic amylase, such as a polypeptide having non-maltogenic exoamylase activity, in particular, glucan 1,4-alpha-maltotetrahydrolase (EC 3.2.1.60) activity (as disclosed in WO05/003339). A suitable non-maltogenic amylase is commercially available as Powersoft™ (available from Danisco A/S, Denmark). Maltogenic amylases such as Novamyl™ (Novozymes A/S, Denmark) may also be used. In one embodiment, the combined use of alpha amylases and the food improver of the invention may be used in a dough, and/or the production of a baked product, such as bread, cakes, doughnuts, cake doughnuts or bagels. The combination of alpha amylases and the food improver of the invention is also considered as preferable for use in methods of production of tortillas, such as wheat and/or maize tortillas.

In another preferred embodiment, the food improver generated according to the present invention may be used in combination with a xylanase in producing food products. GRINDAMYL™ and POWERBake 7000 are examples of commercially available xylanase enzymes available from Danisco A/S. Other examples of xylanase enzymes may be found in WO03/020923 and WO01/42433.

Preferably, the food improver generated according to the present invention may be used in combination with a xylanase and an alpha amylase. Suitably the alpha amylase may be a maltogenic, or a non-maltogenic alpha amylase (such as GRINDAMYLT™ or POWERSoft, commercially available from Danisco A/S), or a combination thereof.

The food improver of the invention can also preferably be used in combination with an oxidising enzyme, such as a maltose oxidising enzyme (MOX), for example hexose oxidase (HOX). Suitable methods are described in WO03/099016. Commercially available maltose oxidising enzymes GRINDAMYL™ and SUREBake are available from Danisco A/S.

Optionally an alpha-amylase, such as a non-maltogenic exoamylase and/or a maltogenic amylases, and/or a maltose oxidising enzyme (MOX) in combination with the enzyme may be used in methods according to the present invention for preparing a dough, a baked product, tortilla, cake, pasta, instant noodle/fried snack food, or a dairy product such as cheese.

The food improver generated according to the present invention is typically included in the foodstuff or other composition by methods known in the art. Such methods include adding the food improver directly to the foodstuff or composition, addition of the food improver in combination with a stabilizer and/or carrier, and addition of a mixture comprising the food improver and a stabilizer and/or carrier.

Suitable stabilizers for use with the present invention include but is not limited to inorganic salts (such as NaCl, ammonium sulphate), sorbitol, emulsifiers and detergents (such as Tween 20, Tween 80, Panodan AB100 without triglycerides, polyglycerolester, sorbitanmonoleate), oil (such as rape seed oil, sunflower seed oil and soy oil), pectin, trehalose, sorbitol and glycerol.

Suitable carriers for use with the present invention include but are not limited to starch, cereal flours, ground wheat, wheat flour, NaCl and citrate.

For baked products, such as bread, steam buns and US white pan bread, for example, the addition of a food improver of the present invention may result in one or more of the following: improved bread volume and softness, prolonged shelf life and/or an antistaling effect, improved crumb structure, reduced pore heterogeneity, reduced mean pore size, enhanced gluten index, improved flavour and/or odour, and improved colour of the crust.

Advantageously, the food improver generated according to the present invention may be used to replace emulsifiers in foodstuffs, such as dough and/or baked products.

The food improver generated according to the present invention may have synergy with emulsifiers such as DATEM, SSL, CSL, monoglyceride, polysorbates and Tween. Thus, the food improver generated according to the present invention may be used in combination with one or more emulsifiers. Advantageously, the use of the food improver generated according to the present invention in combination with one or more emulsifiers may reduce the overall amount of emulsifier used compared with the amount needed when no food improver generated according to the present invention is used.

The food improver generated according to the present invention may also have synergy with hydrocolloids, Guar, xanthum and pectin, and with maltose oxidising enzymes such as hexose oxidase.

For doughnuts, cake doughnuts, bagels, snack cakes and muffins, for example, the use of a food improver of the present invention may result in a synergistic effect when used in combination with one or more of alpha-amylases, maltogenic alpha-amylase and non-maltogenic alpha-amylase.

For cakes, sponge cakes and palm cakes, for example, the use of the food improver of the present invention may result in a synergistic effect when used in combination with one or more of hydrocolloids such as Guar, and/or one or more emulsifiers such as DATEM.

For biscuits, for example, use of a food improver generated according to the present invention confers improved rollability and handling properties, particularly when cold (cold rollability).

Advantageously, in mayonnaise and other egg-based products, for example, use of a food improver generated according to the present invention may lead to improved texture, reduced mean particle size, and/or reduced mean particle distribution, improved heat stability, improved microwave performance and/or stability.

In cakes, use of the present invention advantageously leads to improved softness, volume, improved keeping properties and shelf life.

For noodles or noodle-products, e.g. instant noodles, for example, the food improver of the present invention may confer one or more of the following characteristics: improved colour/yellowness, more stable colour characteristics, reduced brightness, reduced fat content, improved texture and bite (chewiness), reduced water activity, reduced breakage, increased core firmness and improved shape retention during processing.

Preferably, the food improver of the present invention may be used to reduce the fat content of a noodle or a noodle product, for instance an instant noodle.

In tortilla, for example, use of the food improver generated according to the present invention may result in one or more of the following: reduced rollability of the tortilla, for instance by increasing pliability, improved antistaling properties, improving softness and/or reducing off flavour.

Advantageously, improved rollability and/or pliability may lead to a reduced likelihood of the tortilla splitting when rolled.

The food improver generated according to the present invention is particularly useful in the preparation of baked products, such as those prepared from a dough, including breads, cakes, sweet dough products, laminated doughs, liquid batters, muffins, doughnuts, biscuits, crackers and cookies.

The food improver generated according to the present invention is particularly useful in the preparation of breakfast cereals, such as those prepared from a dough.

The food improver may also be used in bread-improving additive, e.g. dough compositions, dough additive, dough conditioners, pre-mixes and similar preparations conventionally added to the flour and/or the dough during processes for making bread or other baked products to provide improved properties to the bread or other baked products.

Thus, the present invention further relates to a bread-improving composition and/or a dough-improving composition comprising a food improver generated according to the present invention; and also to a dough or baked product comprising such a bread-improving and/or dough-improving composition.

The bread-improving composition and/or dough-improving composition may comprise, in addition to a fungal lipolytic enzyme according to the present invention, other substances, which substances are conventionally used in baking to improve the properties of dough and/or baked products.

The bread-improving composition and/or dough-improving composition may comprise one or more conventional baking agents, such as one or more of the following constituents:

A milk powder, gluten, an emulsifier, granulated fat, an oxidant, an amino acid, a sugar, a salt, flour or starch.

Examples of suitable emulsifiers are: monoglycerides, diacetyl tartaric acid esters of mono- and diglycerides of fatty acids, sugar esters, sodium stearoyl lactylate (SSL) and lecithins.

The bread and/or dough improving composition may further comprise another enzyme, such as one or more other suitable food grade enzymes, including starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases, galactolipases, and hexose oxidase, proteases and acyltransferases (such as those described in WO04/064987 for instance).

The term "baked product" as used herein includes a product prepared from a dough. Examples of baked products (whether of white, light or dark type) which may be advantageously produced by the present invention include one or more of the following: bread (including white, whole-meal and rye bread), typically in the form of loaves or rolls or toast, French baguette-type bread, pitta bread, tortillas, tacos, cakes, pancakes, biscuits, crisp bread, pasta, noodles and the like.

The dough in accordance with the present invention may be a leavened dough or a dough to be subjected to leavening. The dough may be leavened in various ways such as by adding sodium bicarbonate or the like, or by adding a suitable yeast culture such as a culture of *Saccharomyces cerevisiae* (baker's yeast).

The dough in accordance with the present invention may be dough for preparation of a dry cereal product, a crisp bread, a biscuit or a cracker.

Specific Embodiments of the Invention

As discussed above, the present invention relates to a method for the treatment of lipid-containing plant material, the method comprising the step of treating a liquid suspension of an at least partly solubilised lipid-containing plant material with one or more lipid modifying enzyme.

In some embodiments, the method further comprises a preceding or simultaneous step of treating a liquid suspension of lipid-containing plant material to obtain said at least partly solubilised plant material.

In some embodiments, the method further comprises a subsequent step of treating said liquid suspension to obtain further solubilised plant material.

In some embodiments, the treatment to obtain an at least partly solubilised plant material is a treatment with one or more cell-wall modifying enzyme.

In some embodiments, the treatment to obtain an at least partly solubilised plant material is a treatment by sonication, such as ultrasonic treatment and/extrusion.

In some embodiments, the at least partly solubilised liquid suspension of plant material contains in-soluble plant material.

In some embodiments, the plant material is treated under said method steps simultaneously.

In some embodiments, the plant material is treated under the method steps according to the present invention without the removal of substantial amount of any component.

In some embodiments, the liquid suspension is further treated with one or more further enzyme.

In some embodiments, the one further enzyme is one or more transglucosylation enzyme.

In some embodiments, the one further enzyme is a protease.

In some embodiments, the one or more lipid modifying enzyme is a lipolytic enzyme selected from the group consisting of: a triacylglycerol lipase, a phospholipase, and a galacto-lipase.

In some embodiments, the one or more lipid modifying enzyme contain two or three activities selected from the group consisting of: triacylglycerol lipase activity, phospholipase activity, and galacto-lipase activity.

In some embodiments, the one or more lipid modifying enzyme is one, two, three, four or five different lipid modifying enzymes.

In some embodiments, the method according to the present invention further comprises a step of isolating the soluble fraction.

In some embodiments, the one or more cell-wall modifying enzyme is selected from the group consisting of a xylanase, and a cellulase, such as cellobiohydrolases, endo-glucanases, and beta-glucanase.

In some embodiments, the cellulase is selected from an endo-cellulase, an exo-cellulase, a cellobiase, an oxidative cellulases, a cellulose phosphorylases.

In some embodiments, the one or more one or more further enzyme is a starch modifying enzyme selected from the group consisting of an alpha-amylase, a pullulanase, isoamylase and a beta-amylase.

In some embodiments, the one or more transglucosylation enzyme is selected from the group consisting of enzymes of enzyme class EC3.2.1.20.

In some embodiments, the plant material is provided in particles, wherein the average particle size of said particulate plant material is below 3000 μm, such as below 1000 μm, such as below 500 μm.

In some embodiments, the plant material is a cereal bran.

In some embodiments, the cereal bran is selected from wheat, barley, oat, rye, triticale, rice, and corn.

In some embodiments, the method according to the present invention further comprises a preceding step of i) fractionating the cereal grain to obtain endosperm, bran, and germ; ii) separating and distributing the endosperm, bran, and germ to allow them to be treated; and iii) milling the bran.

In some embodiments, the cereal bran is obtained from an industrial milling process and further milled to obtain an average particle size below 500 μm, such as below 400 μm, such as below 200 μm.

In some embodiments, the plant material is a side-stream from processing of plant material, such as soap stocks from refining of vegetable oils, brewers spent grain or Destillers dried spent grain with solubles (DDGS).

In some embodiments, the composition obtained comprising modified lipids, such as functional lipids are further treated to inactivate further enzyme activity.

In some embodiments, the solubilisation degree of said plant material as determined on drymatter versus drymatter plant material obtained is higher than 15%, such as higher than 25%, such as higher than 35%, such as higher than 40%, such as higher than 50%, such as in the range of 40%-60%, such as in the range of 50%-60%.

In some embodiments, the total content of lipids and modified lipids, such as functional lipid as determined on drymatter versus drymatter plant material in the soluble fraction obtained is at least about 0.05%, such as at least about 1.0%, such as in the range of 0.05-5%.

In some embodiments, the method according to the present invention further comprises a step of drying the composition obtained comprising lipids and/or modified lipids, such as functional lipids.

In some embodiments, the method according to the present invention further comprises a step of spray drying the composition obtained comprising modified lipids and/or modified lipids, such as functional lipid lipids.

In some embodiments, the method according to the present invention further comprises a step of lyophilisation of the composition obtained comprising lipids and/or modified lipids, such as functional lipid lipids.

In some embodiments, the treatment with one or more lipid modifying enzymes generates functional lipids, such as emulsifiers.

In some embodiments, the treatment with one or more lipid modifying enzymes generates other functional compounds, such as functional sterol esters.

In some embodiments, the treatment with one or more lipid modifying enzymes generates more than 5%, such as more than 10%, such as more than 25%, such as more than 50% conversion of phosphophatidylinositol into lysophosphatidylinositol (lyso-PI).

In some embodiments, the treatment with one or more lipid modifying enzymes hydrolyses at least 5% of the phospholipids, such as at least 10% of the phospholipids, such as at least 20% of the phospholipids, such as at least 50% of the phospholipids, such as 75% of the phospholipids.

In some embodiments, the treatment with one or more lipid modifying enzymes hydrolyses at least 5% of the glycolipids, such as at least 10% of the glycolipids, such as at least 20% of the glycolipids, such as at least 50% of the glycolipids, such as 75% of the glycolipids.

In some embodiments, the treatment with one or more lipid modifying enzymes hydrolyses at least 5% of the triglycerides, such as at least 10% of the triglycerides, such as at least 20% of the triglycerides, such as at least 50% of the triglycerides, such as 75% of the triglycerides.

In some embodiments, the composition comprising lipids and/or modified lipids, such as functional lipid obtained in the method according to the invention is added directly as a mixture of soluble and insoluble plant material in the production of the food product.

In some embodiments, the food product according to the present invention is selected from the group consisting of bread, a breakfast cereal, a pasta, biscuits, cookies, snacks, and beer.

smaller particle size might be preferable, regarding the degree of solubilisation.

Enzymes:

TABLE 1

Enzymes used for wheat bran modification

| Enzyme Activity | Enzyme ID |
| --- | --- |
| Xylanase | Bacterial xylanase |
| Cellulase/glucanase | Genencor GC220 |
| Amylase | Genencor, Spezyme Fred (4016101001) |
| Pullulanase | Genencor Optimax L-1000 (401-05349-002) |
| Beta-amylase | Genencor Optimalt BBA (EDS 221) |
| Phospho-galacto lipase | Grindamyl Powerbake 4070 |
| Transglucosidase | Genencor TGL-500 (1600675782) |

Protocol:

TABLE 2

Protocol used for bran modification

Wheat bran is suspended in 50 mM NaPi, pH 5 (13% w/w) in a container/reactor with closed lid
The Bran suspension is heated to 100 dg C. under stirring, and boiled for 2 min
Sample is placed under stirring (with closed lid) at 50 dg C. and left to equilibrate in regard to temp
Enzymes are added and reaction is continued @ 50 dg C. for 24 h (Temp and time may be further optimised)
Supernatant is separated from residual solids
Supernatant is boiled to inactivate further enzyme activity
Sample cooled and stored to avoid contamination
Pellet is freeze dried
Supernatant is analysed Trials:
    The following modifications was made to the bran (table 3)

TABLE 3

Amount of bran, g, treated with different enzymes

| | | | Gram enzyme sample/10 g bran | | | | | | |
| --- | --- | --- | --- | --- | --- | --- | --- | --- | --- |
| Trial | Bran, g | Buffer, g | Xylanase | GC220 | Amylase | Pullulanase | Beta-amylase | Transglu. | Phospholipase |
| 1 | 10 | 66.7 | 1.12 | 0.05 | 0.04 | 0.01 | 0.01 | 0.05 | — |
| 2 | 10 | 66.7 | 1.12 | 0.05 | 0.04 | 0.01 | 0.01 | 0.05 | 0.000002 |
| 3 | 10 | 66.7 | 1.12 | 0.05 | 0.04 | 0.01 | 0.01 | 0.05 | 0.000017 |
| 4 | 10 | 66.7 | 1.12 | 0.05 | 0.04 | 0.01 | 0.01 | 0.05 | 0.000172 |

EXAMPLES

Example 1

Labscale Modification of Commercial Wheat Bran and Wheat Bran Lipids Followed by Evaluation in Baking Bran:
    Wheat bran fractions obtained from a commercial mill was used. The fractions consisted of a fine bran fraction and a course bran fraction. Before use, the course bran fraction was milled to obtains a smaller particle size, which will increase the specific surface of the bran, eventually increase the efficiency of the enzymatic solubilisation of the bran. The milling was conducted on a Retch mill to obtain an average particle size of 500 μm. However, it should be noted that a Analysis:
    The soluble bran fraction (the supernatant) is analysed in regard to:

Dry matter content (%):
    A quantitative sample of the soluble bran obtained is lyophilised. After lyophilisation, the sample size is quantified again and the amount of drymatter is calculated. As a blank, the buffer is included in this analysis.

Evaluation of Lipid Modification Using Baking Trials:

Baking Recipe:
    The baking performance of the flour, flour added modified solubilised bran was evaluated in small scale baking trials (50 gram mixer and 10 gram loaves) using the below recipe (table 4).

TABLE 4

Recipe used for evaluating the baking performance of flour, flour added solubilised bran and the reconstituted flour added unsolubilised bran.

| Ingredients | Mini scale ml or g |
| --- | --- |
| Flour | 50 |
| Dry yeast | 1 |
| Salt/Sugar | 1.6 |
| Water | 400 BU - 2% |

Salt/sugar is a 1:1 (w/w) mixture of salt and sugar. Water is the water absorption determined by Farinograph analysis.

Dough Making and Baking

The flour (or mix of flour and bran) and dry ingredients are mixed for one minute, hereafter water was added and mixing was continued for another five minutes.

After mixing, four dough lumps were weighed out, each containing 10 gram flour. These were moulded into bread using a hand-moulder. Loaves were put into baking pans and placed in a sealed container (with a lid) and left on the table for 10 minutes. Hereafter, bread is proofed at 34° C. 85% RH for 45 minutes and finally baked at 230° C. for five minutes in a Bago oven (Bago-line, Fåborg, Denmark). During scaling of the dough, the stickiness was subjectively evaluated on a scale from 1 (very sticky) to 5 (dry).

The bread was cooled for 20 minutes before evaluation (weighing, volume measurement, and crumb, crust and sensoric evaluation).

Baking Trials

The below baking trials were conducted (table 5).

TABLE 5

Baking trial experimental setup.

| Baking ID | | Flour, g | Bran, g | Sol. Bran, g | Water, ml | "Bran", % in flour |
| --- | --- | --- | --- | --- | --- | --- |
| 1 | Blank | 50 | 0 | 0 | 29.00 | — |
| 2 | Sol bran 5.0% (1) | 50 | 0 | 29.00 | — | 5.22 |
| 3 | Sol bran 5.0%, 1 TIPU (2) | 50 | 0 | 29.00 | — | |
| 4 | Sol bran 5.0%, 10 TIPU (3) | 50 | 0 | 29.00 | — | |
| 5 | Sol bran 5.0%, 100 TIPU (4) | 50 | 0 | 29.00 | — | |
| 6 | 5.0% Bran | 47.5 | 2.5 | — | 29.00 | 5.00 |

ID refers to flour composition either added solubilised bran or reconstituted with insoluble bran, number in brackets refers to bran treatment according to table 3.
Flour (g) is the amount of flour flour in the bread.
Bran (g) is the amount of bran used for reconstitution.
Sol. Bran (ml) is the amount of solubilised bran added to the flour instead of water.
Water (ml) is the amount of water added to the flour.
"Bran", (%) is the amount of bran, either solubilised or as insoluble bran based on flour weight.
TIPU refers to Titration Phospholipase Unit as described above.

Results:

Bran Solubilisation Degree:

Based on drymatter, the amount of bran solubilised in the trials was approx. 54%.

Baking Results:

As can be seen in table 6 and FIG. 1, the addition of the soluble fibers had little to no effect on the specific volume of the bread. However, combining the solubilisation of the bran with the phospholipase, have a significant effect on the bread volume

TABLE 6

Baking trial results.

| Baking | ID | Spec. Vol, ml/g | Rel vol vs blank |
| --- | --- | --- | --- |
| 1 | Blank | 3.58 | 100 |
| 2 | Sol bran 5.0% | 3.46 | 97 |
| 3 | Sol bran 5.0%, 1TIPU | 4.05 | 113 |
| 4 | Sol bran 5.0%, 10TIPU | 4.24 | 118 |
| 5 | Sol bran 5.0%, 100TIPU | 4.97 | 139 |
| 6 | 5.0% Bran | 3.38 | 94 |

ID refers to flour composition, either added solubilised bran or reconstituted with insoluble bran. Flour (g) is the amount of flour flour in the bread. Bran (g) is the amount of bran used for reconstitution. Spec. Vol. (mg/ml) is the absolute specific volumen of the breads. Rel vol vs blank (%) is the relative volume of the breads versus bread 1 (blank)

The resulting breads can be seen in FIG. 2

Example 2

Labscale Modification of Commercial Wheat Bran Lipids Followed by Evaluation in Baking To evaluate the effect of modification of the lipid fraction, generating functional lipids with emulsifying properties. Another experiment using different doses and different lipases was conducted Bran:

Wheat bran fractions obtained from a commercial mill was used. The fractions consisted of a fine bran fraction and a course bran fraction. Before use, the course bran fraction was milled to obtains a smaller particle size, which will increase the specific surface of the bran, eventually increase the efficiency of the enzymatic solubilisation of the bran. The milling was conducted on a Retch mill to obtain an average particle size of 500 μm. However, it should be noted that a smaller particle size might be preferable, regarding the degree of solubilisation.

Enzymes:

TABLE 7

Enzymes used for wheat bran modification

| Enzyme Activity | Enzyme ID |
| --- | --- |
| Phospho-galacto lipase | Grindamyl Powerbake 4070 |
| Lipase | EDS 321 |

Protocol:

TABLE 8

Protocol used for bran modification

Wheat bran is suspended in 50 mM NaPi, pH 5 (13% w/w) in a container/reactor with closed lid
The Bran suspension is heated to 100 dg C. under stirring, and boiled for 2 min
Sample is placed under stirring (with closed lid) at 50 dg C. and left to equilibrate in regard to temp
Enzymes are added and reaction is continued @ 50 dg C. for 24 h (Temp and time may be further optimised)
Supernatant is separated from residual solids
Supernatant is boiled to inactivate further enzyme activity
Sample cooled and stored to avoid contamination
Pellet is freeze dried
Supernatant is analysed Trials:

The following modifications was made to the bran (table 9)

TABLE 9

Amount of bran, g, treated with different enzymes

| Trial | Bran, g | Buffer, g | Gram enzyme sample/10 g bran | |
|---|---|---|---|---|
| | | | Phospholipase | Lipase |
| 1 | 10 | 66.7 | 0.000017 | |
| 2 | 10 | 66.7 | 0.000172 | |
| 3 | 10 | 66.7 | | 7.28E−09 |
| 4 | 10 | 66.7 | | 7.28E−08 |
| 5 | 10 | 66.7 | | 7.28E−07 |
| 6 | 10 | 66.7 | 0.000017 | 7.28E−08 |

Analysis:

The soluble bran fraction (the supernatant) is analysed in regard to:

Dry matter content (%):

A quantitative sample of the soluble bran obtained is lyophilised. After lyophilisation, the sample size is quantified again and the amount of drymatter is calculated. As a blank, the buffer is included in this analysis.

Evaluation of Lipid Modification Using Baking Trials:

Baking Recipe:

The baking performance of the flour, flour added modified solubilised bran was evaluated in small scale baking trials (50 gram mixer and 10 gram loaves) using the below recipe (table 10).

TABLE 10

Recipe used for evaluating the baking performance of flour, flour added solubilised bran and the reconstituted flour added unsolubilised bran.

| Ingredients | Mini scale ml or g |
|---|---|
| Flour | 50 |
| Dry yeast | 1 |
| Salt/Sugar | 1.6 |
| Water | 400 BU - 2% |

Salt/sugar is a 1:1 (w/w) mixture of salt and sugar. Water is the water absorption determined by Farinograph analysis.

Dough Making and Baking

The flour (or mix of flour and bran) and dry ingredients are mixed for one minute, hereafter water was added and mixing was continued for another five minutes.

After mixing, four dough lumps were weighed out, each containing 10 gram flour. These were moulded into bread using a hand moulder. Loaves were put into baking pans and placed in a sealed container (with a lid) and left on the table for 10 minutes. Hereafter, bread is proofed at 34° C. 85% $R^H$ for 45 minutes and finally baked at 230° C. for five minutes in a Bago oven (Bago-line, Fåborg, Denmark). The bread was cooled for 20 minutes before evaluation (weighing, volume measurement, and crumb, crust and sensoric evaluation).

Baking Trials

The below baking trials were conducted (table 11).

TABLE 11

Baking trial experimental setup.

| Baking | ID | Flour, g | Bran extract, ml | Water, ml |
|---|---|---|---|---|
| 1 | Blank | 50 | 0 | 28 |
| 2 | Bran lipid blank | 50 | 29.00 | — |
| 3 | Bran lipid 10 TIPU (1) | 50 | 29.00 | — |
| 4 | Bran lipid 100 TIPU (2) | 50 | 29.00 | — |
| 5 | Bran lipid 3 LIPU (3) | 50 | 29.00 | — |
| 6 | Bran lipid 30 LIPU (4) | 50 | 29.00 | — |
| 7 | Bran lipid 300 LIPU (5) | 50 | 29.00 | — |
| 8 | Bran lipid 10TIPI + 3 LIPU (6) | 50 | 29.00 | — |

ID refers to flour composition added solubilised bran, number in brackets refer to bran treatment according to table 9. Flour (g) is the amount of flour flour in the bread. Bran extract (ml) is the amount of solubilised bran added to the flour instead of water. Water (ml) is the amount of water added to the flour.

Results:

Bran Solubilisation Degree:

Based on drymatter, the amount of bran solubilised in the trials were approx. 30%.

Baking Results:

As can be seen in table 12 and FIG. 3, the addition of the soluble fibers had little to no effect on the specific volume of the bread. However, combining the solubilisation of the bran with the phospholipase, have a significant effect on the bread volume

TABLE 12

Baking trial results.

| Baking | ID | Spec. Vol, ml/g | Rel vol vs blank |
|---|---|---|---|
| 1 | Blank | 3.39 | 100 |
| 2 | Bran lipid blank | 3.16 | 93 |
| 3 | Bran lipid 10 TIPU (1) | 3.29 | 97 |
| 4 | Bran lipid 100 TIPU (2) | 3.44 | 101 |
| 5 | Bran lipid 3 LIPU (3) | 3.18 | 94 |
| 6 | Bran lipid 30 LIPU (4) | 3.20 | 94 |
| 7 | Bran lipid 300 LIPU (5) | 3.29 | 97 |
| 8 | Bran lipid 10TIPI + 3 LIPU (6) | 3.52 | 104 |

ID refers to flour composition added solubilised bran, number in brackets refer to bran treatment according to table 9. Flour (g) is the amount of flour flour in the bread. Spec. Vol. (mg/ml) is the absolute specific volumen of the breads. Rel vol vs blank (%) is the relative volume of the breads versus bread 1 (blank)

The resulting breads can be seen in FIG. 4.

As can be seen from the above results in experiment 2, no significant effect was obtained on the baking performance in this experiment. Compared to example 1, the setup in example 2 differed in the absence of cell wall and starch modifying enzymes. It can thus be concluded that there must be a synergistic effect between cell wall-starch and lipid modifying enzymes in regard to generation of functional lipids from the wheat bran.

Example 3

Labscale Modification of Commercial Wheat Bran and Wheat Bran Lipids Followed by Evaluation in Baking—2

To further evaluate the synergistic effect from modifying wheat bran with cell wall-, starch and lipid modifying enzymes, this experiment was conducted Bran:

Wheat bran fractions obtained from a commercial mill was used. The fractions consisted of a fine bran fraction and a course bran fraction. Before use, the course bran fraction was milled to optains a smaller particle size, which will increase the specific surface of the bran, eventually increase the efficiency of the enzymatic solubilisation of the bran. The milling was conducted on a Retch mill to obtain an average particle size of 500 µm. However, it should be noted that a smaller particle size might be preferable, regarding the degree of solubilisation.

Enzymes:

TABLE 13

Enzymes used for wheat bran modification

| Enzyme Activity | Enzyme ID |
|---|---|
| Xylanase | Bacterial xylanase |
| Cellulase/glucanase | Genencor GC220 |
| Amylase | Genencor, Spezyme Fred (4016101001) |
| Phospho-galacto lipase | Grindamyl Powerbake 4070 |

Protocol:

TABLE 14

Protocol used for bran modification

Wheat bran is suspended in 50 mM NaPi, pH 5 (13% w/w) in a container/reactor with closed lid
The Bran suspension is heated to 100 dg C. under stirring, and boiled for 2 min
Sample is placed under stirring (with closed lid) at 50 dg C. and left to equilibrate in regard to temp
Enzymes are added and reaction is continued @ 50 dg C. for 24 h (Temp and time may be further optimised)
Supernatant is separated from residual solids
Supernatant is boiled to inactivate further enzyme activity
Sample cooled and stored to avoid contamination
Pellet is freeze dried
Supernatant is analysed Trials:

The following modifications was made to the bran (table 15)

TABLE 15

Amount of bran, g, treated with different enzymes

| Trial | Bran, g | Buffer, g | Xylanase | GC220 | Amylase | Phospholipase |
|---|---|---|---|---|---|---|
| 1 | 10 | 66.7 | | | | |
| 2 | 10 | 66.7 | | | | 0.000172 |
| 3 | 10 | 66.7 | 1.12 | 0.05 | | 0.000172 |
| 4 | 10 | 66.7 | 1.12 | 0.05 | 0.04 | 0.000172 |
| 5 | 10 | 66.7 | 1.12 | 0.05 | | 0.000172 |
| 6 | 10 | 66.7 | | | 0.04 | 0.000172 |
| 7 | 10 | 66.7 | | | | 0.000172 |

Analysis:

The soluble bran fraction (the supernatant) is analysed in regard to:

Dry matter content (%):

A quantitative sample of the soluble bran obtained is lyophilised. After lyophilisation, the sample size is quantified again and the amount of drymatter is calculated. As a blank, the buffer is included in this analysis.

Evaluation of Lipid Modification Using Baking Trials:
Baking Recipe:

The baking performance of the flour, flour added modified solubilised bran was evaluated in small scale baking trials (50 gram mixer and 10 gram loaves) using the below recipe (table 16).

TABLE 16

Recipe used for evaluating the baking performance of flour, flour added solubilised bran and the reconstituted flour added unsolubilised bran.

| Ingredients | Mini scale ml or g |
|---|---|
| Flour | 50 |
| Dry yeast | 1 |
| Salt/Sugar | 1.6 |
| Water | 400 BU - 2% |

Salt/sugar is a 1:1 (w/w) mixture of salt and sugar. Water is the water absorption determined by Farinograph analysis.

Dough Making and Baking

The flour (or mix of flour and bran) and dry ingredients are mixed for one minute, hereafter water was added and mixing was continued for another five minutes.

After mixing, four dough lumps were weighed out, each containing 10 gram flour. These were moulded into bread using a hand moulder. Loaves were put into baking pans and placed in a sealed container (with a lid) and left on the table for 10 minutes. Hereafter, bread is proofed at 34° C. 85% RH for 45 minutes and finally baked at 230° C. for five minutes in a Bago oven (Bago-line, Fåborg, Denmark). The bread was cooled for 20 minutes before evaluation (weighing, volume measurement, and crumb, crust and sensoric evaluation).

Baking Trials

The below baking trials were conducted (table 17).

TABLE 17

Baking trial experimental setup.

| Baking | ID | Flour, g | Extra enz, mg/kg | Bran extract, ml | Water, ml |
|---|---|---|---|---|---|
| 1 | Blank | 50 | | 0 | 28 |
| 2 | Bran blank (1) | 50 | | 0 | 29 |
| 3 | Bran BS3, KLM1 (2) | 50 | | 29 | |
| 4 | Bran BS3, GC 220, KLM1 (3) | 50 | | 29 | |
| 5 | Bran BS3, GC220, Spezyme, KLM1 (4) | 50 | | 29 | |
| 6 | Bran GC220, KLM1 (5) | 50 | | 29 | |
| 7 | Bran Spezyme, KLM1 (6) | 50 | | 29 | |
| 8 | Bran KLM1 (7) | 50 | | 29 | |
| 9 | Bran, BS3, GC220, Spezyme, KLM1 (+BS3, KLM1) | 50 | 0.2 + 0.5 | 29 | |

ID refers to flour composition added solubilised bran, number in brackets refer to bran treatment according to table 15. Flour (g) is the amount of flour flour in the bread. Bran extract (ml) is the amount of solubilised bran added to the flour instead of water. Water (ml) is the amount of water added to the flour. Baking No. 9 is a repetetion of Baking 5 however, further added 0.2 mg xylanase and 0.5 mg of phospholipase/kg of flour during dough mixing.

Results:
Bran Solubilisation Degree:

Based on drymatter, the amount of bran solubilised in the trials were in the range of approx. 30 to 54%.

Baking Results:

As can be seen in table 18 and FIG. 5, the addition of the soluble fibers had little to no effect on the specific volume of the bread. However, combining the solubilisation of the bran with the phospholipase, have a significant effect on the bread volume.

TABLE 18

Baking trial results.

| Baking | ID | Spec. Vol, ml/g | Rel vol vs bran blank |
|---|---|---|---|
| 1 | Blank | 3.38 | 110 |
| 2 | Bran blank (1) | 3.08 | 100 |
| 3 | Bran BS3, KLM1 (2) | 3.14 | 102 |
| 4 | Bran BS3, GC 220, KLM1 (3) | 3.57 | 116 |
| 5 | Bran BS3, GC220, Spezyme, KLM1 (4) | 3.84 | 125 |
| 6 | Bran GC220, KLM1 (5) | 3.57 | 116 |
| 7 | Bran Spezyme, KLM1 (6) | 3.26 | 106 |
| 8 | Bran KLM1 (7) | 3.10 | 101 |
| 9 | Bran, BS3, GC220, Spezyme, KLM1 (+BS3, KLM1) | 4.98 | 162 |

ID refers to flour composition added solubilised bran, number in brackets refers to bran treatment according to table 15. Flour (g) is the amount of flour flour in the bread. Spec. Vol. (mg/ml) is the absolute specific volumen of the breads. Rel vol vs blank (%) is the relative volume of the breads versus bread 1 (blank)

The resulting breads can be seen in FIG. 6

As can be seen from the above results in experiment 3, a significant effect was obtained on the baking performance in this experiment by combining the cell wall, starch and lipid modifying enzyme treatment of the bran.

Example 4

Labscale Modification of Commercial Wheat Bran and Wheat Bran Lipids Followed by Evaluation of the Modified Bran in Baking To further evaluate the synergistic effect from modifying wheat bran with cell wall-, starch and lipid modifying enzymes, we want to test the effect of in situ generation of modified lipids having emulsification properties, on the addition of wheat bran in regard to baking performance. It is well known that bran addition to flour, or whole grain flour, has less baking potential than endosperm flour.

Bran:

Wheat bran fractions obtained from a commercial mill was used. The fractions consisted of a fine bran fraction and a course bran fraction. Before use, the course bran fraction was milled to obtain a smaller particle size, which will increase the specific surface of the bran, eventually increase the efficiency of the enzymatic solubilisation of the bran. The milling was conducted on a Retch mill to obtain an average particle size of 500 μm. However, it should be noted that a smaller particle size might be preferable, regarding the degree of solubilisation.

Enzymes:

TABLE 19

Enzymes used for wheat bran modification

| Enzyme Activity | Enzyme ID |
|---|---|
| Xylanase | Danisco Bacterial xylanase (1223449, 4010866762) |
| Cellulase/glucanase | Genencor GC220 |
| Amylase | Genencor, Spezyme Fred (4016101001) |
| Phospho-galacto lipase | Danisco Grindamyl Powerbake 4070 |

Protocol:

Table 20. Protocol used for bran modification

Wheat bran is suspended in 50 mM NaPi, pH 5 (13% w/w) in a container/reactor with closed lid The Bran suspension is heated to 100 dg C under stirring, and boiled for 2 min Samples are placed under stirring (with closed lid) at 50 dg C and left to equilibrate in regard to temp Enzymes are added and reaction is continued @ 50 dg C for 24 h (Temp and time may be further optimised)

The modified bran is boiled to inactivate further enzyme activity

Samples are cooled and stored to avoid contamination

Trials:

The following modifications was made to the bran (table 21)

TABLE 21

Amount of bran, g, treated with different enzymes

| | | | gram enzyme sample/10 g bran | | | |
|---|---|---|---|---|---|---|
| Trial | Bran, g | Buffer, g | Xylanase | GC220 | Amylase | Danisco Phospho-galactolipase |
| 1 | 10 | 66.7 | 0.19 | 0.05 | 0.04 | |
| 2 | 10 | 66.7 | 0.19 | 0.05 | 0.04 | 0.0003 |

Evaluation of Lipid Modification Using Baking Trials:

Baking Recipe:

The baking performance of the flour and flour added modified bran was evaluated in small scale baking trials (50 gram mixer and 10 gram loaves) using the below recipe (table 22).

TABLE 22

Recipe used for evaluating the baking performance of flour, and flour added modified bran and.

| Ingredients | Mini scale ml or g |
|---|---|
| Flour | 50 |
| Dry yeast | 1 |
| Salt/Sugar | 1.6 |
| Water | 400 BU - 2% |

Salt/sugar is a 1:1 (w/w) mixture of salt and sugar. Water is the water absorption determined by Farinograph analysis.

Dough Making and Baking

The flour and dry ingredients are mixed for one minute, hereafter water (or water and modified bran) was added and mixing was continued for another five minutes.

After mixing, four dough lumps were weighed out, each containing 10 gram flour. These were moulded into bread using a hand moulder. Loaves were put into baking pans and placed in a sealed container (with a lid) and left on the table for 10 minutes. Hereafter, bread is proofed at 34° C. 85% $R^H$ for 45 minutes and finally baked at 230° C. for five minutes in a Bago oven (Bago-line, Fåborg, Denmark). The bread was cooled for 20 minutes before evaluation (weighing, volume measurement, and crumb, crust and sensoric evaluation).

Baking Trials

The below baking trials were conducted (table 23).

TABLE 23

Baking trial experimental setup.

| Baking | ID | Flour, g | Bran extract, ml | Water, ml |
|---|---|---|---|---|
| 1 | Blank (wheat) | 50 | 0 | 29 |
| 2 | W Bran cell wall enz (with insolubles) (1) | 50 | 30 | 0 |

TABLE 23-continued

Baking trial experimental setup.

| Baking | ID | Flour, g | Bran extract, ml | Water, ml |
|---|---|---|---|---|
| 3 | W Bran cell wall enz (with insolubles) + Lipase (with insol) (2) | 50 | 30 | 0 |

ID refers to dough composition, number in brackets refers to bran treatment according to table 21. Flour (g) is the amount of flour in the bread. Bran extract (ml) is the amount of solubilised bran added to the flour instead of water. Water (ml) is the amount of water added to the flour.

Results:
Baking Results:

As can be seen in table 24 and FIG. 7, the addition of the modified fibers had a negative effect on the specific volume of the bread. However, addition of bran also modified with the phospholipase, generating functional lipids, having a much less detrimental effect on the bread volume compared to just adding cell wall modified bran.

TABLE 24

Baking trial results.

| Baking | ID | Spec. Vol, ml/g | Rel vol vs blank |
|---|---|---|---|
| 1 | Blank (wheat) | 3.40 | 100 |
| 2 | W Bran cell wall enz (with insolubles) (1) | 3.14 | 92 |
| 3 | W Bran cell wall enz (with insolubles) + Lipase (with insol) (2) | 3.51 | 103 |

ID refers to dough composition, number in brackets refers to bran treatment according to table 21. Flour (g) is the amount of flour in the bread. Spec. Vol. (mg/ml) is the absolute specific volumen of the breads. Rel vol vs blank (%) is the relative volume of the breads versus bread 1 (blank)

The resulting breads can be seen in FIG. 7

As can be seen from the above results, a significant effect was obtained on the baking performance in this experiment by combining the cell wall, starch and lipid modifying enzyme treatment of the bran before addition to the dough.

Example 5

Labscale Modification of Rice Bran and Rice Bran Lipids Followed by Evaluation of the Solubilised Bran and Modified Bran Lipids in Baking To further evaluate our surprising findings regarding bran solubilisation combined with modification of bran lipids, we want to test the effect of solubilised rice bran and modified rice bran lipids in baking trials.

Bran:
Commercial rice bran fraction was used for the experiment.

Enzymes:

TABLE 25

Enzymes used for wheat bran modification

| Enzyme Activity | Enzyme ID |
|---|---|
| Xylanase | Danisco Bacterial xylanase (1223449, 4010866762) |
| Cellulase/glucanase | Genencor GC220 |

TABLE 25-continued

Enzymes used for wheat bran modification

| Enzyme Activity | Enzyme ID |
|---|---|
| Amylase | Genencor, Spezyme Fred (4016101001) |
| Phospho-galacto lipase | Danisco Grindamyl Powerbake 4070 |

Protocol:
Table 26. Protocol Used for Bran Modification

Rice bran is suspended in 50 mM NaPi, pH 5 (13% w/w) in a container/reactor with closed lid The Bran suspension is heated to 100 dg C under stirring, and boiled for 2 min Sample is placed under stirring (with closed lid) at 50 dg C and left to equilibrate in regard to temp Enzymes are added and reaction is continued @ 50 dg C for 24 h (Temp and time may be further optimised)

Supernatant is separated from residual solids

Supernatant is boiled to inactivate further enzyme activity

Sample cooled and stored to avoid contamination

Trials:

The following modifications was made to the rice bran (table 27)

TABLE 27

Amount of rice bran, g, treated with different enzymes

| | | | gram enzyme sample/10 g bran | | | |
|---|---|---|---|---|---|---|
| Trial | Bran, g | Buffer, g | Xylanase | GC220 | Amylase | Danisco Phospho-galactolipase |
| 1 | 10 | 66.7 | 0.19 | 0.05 | 0.04 | |
| 2 | 10 | 66.7 | 0.19 | 0.05 | 0.04 | 0.0003 |

Evaluation of Lipid Modification Using Baking Trials:
Baking Recipe:

The baking performance of the flour and flour added solubilised bran and/or modified lipids was evaluated in small scale baking trials (50 gram mixer and 10 gram loaves) using the below recipe (table 28).

TABLE 28

Recipe used for evaluating the baking performance different dough compositions (+/−solubilised bran).

| Ingredients | Mini scale ml or g |
|---|---|
| Flour | 50 |
| Dry yeast | 1 |
| Salt/Sugar | 1.6 |
| Water | 400 BU - 2% |

Salt/sugar is a 1:1 (w/w) mixture of salt and sugar. Water is the water absorption determined by Farinograph analysis.

Dough Making and Baking

The flour and dry ingredients are mixed for one minute, hereafter water was added and mixing was continued for another five minutes.

After mixing, four dough lumps were weighed out, each containing 10 gram flour. These were moulded into bread using a hand moulder. Loaves were put into baking pans and placed in a sealed container (with a lid) and left on the table for 10 minutes. Hereafter, bread is proofed at 34° C. 85% RH for 45 minutes and finally baked at 230° C. for five minutes in a Bago oven (Bago-line, Fåborg, Denmark). The bread was cooled for 20 minutes before evaluation (weighing, volume measurement, and crumb, crust and sensoric evaluation).

Baking Trials

The below baking trials were conducted (table 29).

TABLE 29

Baking trial experimental setup.

| Bagning | ID | Flour, g | Bran extract, ml |
|---|---|---|---|
| 1 | Blank (wheat) | 50 | 0 |
| 2 | R Bran cell wall enz (1) | 50 | 30 |
| 3 | R Bran cell wall enz + Lipase (2) | 50 | 30 |

ID refers to dough composition, number in brackets refer to bran treatment according to table 27. Flour (g) is the amount of flour in the bread. Bran extract (ml) is the amount of solubilised bran added to the flour instead of water. Water (ml) is the amount of water added to the flour.

Results:
Baking Results:

As can be seen in table 30 and FIG. 8 below, the addition of the modified soluble fibers had no negative effect the specific volume of the bread, actually a positive effect in regard to bread volume. However, addition of the modified soluble fibers also modified with the phospholipase, generating functional lipids, have a much better effect on the bread volume compared to just adding modified soluble fibers.

TABLE 30

Baking trial results.

| Bagning | ID | Spec. Vol, ml/g | Rel vol vs blank |
|---|---|---|---|
| 1 | Blank (wheat) | 3.40 | 100 |
| 2 | R Bran cell wall enz (1) | 4.16 | 123 |
| 3 | R Bran cell wall enz + Lipase (2) | 4.54 | 134 |

ID refers to dough composition, number in brackets refers to bran treatment according to table 27. Flour (g) is the amount of flour in the bread. Spec. Vol. (mg/ml) is the absolute specific volumen of the breads. Rel vol vs blank (%) is the relative volume of the breads versus bread 1 (blank)

The resulting breads can be seen in FIG. 8

As can be seen from the above results, a significant effect was obtained on the baking performance in this experiment by adding soluble bran and modified lipids obtained by combining the cell wall, starch and lipid modifying enzyme treatment of the rice bran before.

Example 6

Labscale Modification of Commercial Wheat Bran and Wheat Bran Lipids, Using Different Lipases, Followed by Evaluation in Baking To further evaluate our surprising findings regarding bran solubilisation combined with modification of bran lipids, we want to test other lipases than the Danisco Phospho-galacto lipase, followed by evaluation of the modified lipids generated in baking trials.

Bran:

Wheat bran fractions obtained from a commercial mill was used. The fractions consisted of a fine bran fraction and a course bran fraction. Before use, the course bran fraction was milled to obtain a smaller particle size, which will increase the specific surface of the bran, eventually increase the efficiency of the enzymatic solubilisation of the bran. The milling was conducted on a Retch mill to obtain an average particle size of 500 μm. However, it should be noted that a smaller particle size might be preferable, regarding the degree of solubilisation.

Enzymes:

TABLE 31

Enzymes used for wheat bran modification

| Enzyme Activity | Enzyme ID |
|---|---|
| Xylanase | Danisco Bacterial xylanase (1223449, 4010866762) |
| Cellulase/glucanase | Genencor GC220 |
| Amylase | Genencor, Spezyme Fred (4016101001) |
| Phospho-galacto lipase | Danisco Grindamyl Powerbake 4070 (Danisco) |
| Phospho-galacto lipase | Novozymes Lipopan F (Lipopan F) |
| Phospho-galacto lipase | DSM's Panamore (Panamore) |

Protocol:

TABLE 32

Protocol used for bran modification

Wheat bran is suspended in 50 mM NaPi, pH 5 (13% w/w) in a container/reactor with closed lid
The Bran suspension is heated to 100 dg C. under stirring, and boiled for 2 min
Sample is placed under stirring (with closed lid) at 50 dg C. and left to equilibrate in regard to temp
Enzymes are added and reaction is continued @ 50 dg C. for 24 h (Temp and time may be further optimised)
Supernatant is separated from residual solids
Supernatant is boiled to inactivate further enzyme activity
Sample cooled and stored to avoid contamination Trials:

The following modifications was made to the bran (table 33)

TABLE 33

Amount of bran, g, treated with different enzymes

| | Bran, | Buffer, | gram enzyme sample/10 g bran | | | |
|---|---|---|---|---|---|---|
| Trial | g | g | Xylanase | GC220 | Amylase | Phospholipase |
| 1 | 10 | 66.7 | | | | |
| 2 | 10 | 66.7 | 0.19 | 0.05 | 0.04 | |
| 3 | 10 | 66.7 | 0.19 | 0.05 | 0.04 | 0.0003 (Danisco) |
| 4 | 10 | 66.7 | 0.19 | 0.05 | 0.04 | 0.00013 (Lipopan F) |
| 5 | 10 | 66.7 | 0.19 | 0.05 | 0.04 | 0.0002 (Panamore) |

Evaluation of Lipid Modification Using Baking Trials:

Baking Recipe:

The baking performance of the flour, flour added modified solubilised bran (+/− modified lipids) was evaluated in small scale baking trials (50 gram mixer and 10 gram loaves) using the below recipe (table 34).

TABLE 34

Recipe used for evaluating the baking performance of flour, flour added solubilised bran and flour added solubilised bran and modified lipids.

| Ingredients | Mini scale ml or g |
|---|---|
| Flour | 50 |
| Dry yeast | 1 |
| Salt/Sugar | 1.6 |
| Water | 400 BU - 2% |

Salt/sugar is a 1:1 (w/w) mixture of salt and sugar. Water is the water absorption determined by Farinograph analysis.

Dough Making and Baking

The flour and dry ingredients are mixed for one minute, hereafter water was added and mixing was continued for another five minutes.

After mixing, four dough lumps were weighed out, each containing 10 gram flour. These were moulded into bread using a hand moulder. Loaves were put into baking pans and placed in a sealed container (with a lid) and left on the table for 10 minutes. Hereafter, bread is proofed at 34° C. 85% RH for 45 minutes and finally baked at 230° C. for five minutes in a Bago oven (Bago-line, Fåborg, Denmark). The bread was cooled for 20 minutes before evaluation (weighing, volume measurement, and crumb, crust and sensoric evaluation).

Baking Trials

The below baking trials were conducted (table 35).

TABLE 35

Baking trial experimental setup.

| Baking | ID | Flour, g | Bran extract, ml | Water, ml |
|---|---|---|---|---|
| 1 | Blank (wheat) | 50 | 0 | 29 |
| 2 | W Bran cell wall enz (1) | 50 | 30 | |
| 3 | W Bran cell wall enz + Danisco (2) | 50 | 30 | |
| 4 | W Bran cell wall enz + Lipopan F (3) | 50 | 30 | |
| 5 | W Bran cell wall enz + Panamore (4) | 50 | 30 | |

ID refers to dough composition, number in brackets refers to bran treatment according to table 33. Flour (g) is the amount of flour in the bread. Bran extract (ml) is the amount of solubilised bran added to the flour instead of water. Water (ml) is the amount of water added to the flour.

Results:

Baking Results:

As can be seen in table 36 and FIG. 9, the addition of the soluble fibers had little to no effect on the specific volume of the bread. However, combining the solubilisation of the bran with the phospholipase, have a significant effect on the bread volume, all bread baked with bran treated with the lipases in combination with cell wall- and starch modifying enzymes, had a volume increase compared to flour control.

TABLE 36

Baking trial results.

| Bagning | ID | Spec. Vol, ml/g | Rel vol vs blank |
|---|---|---|---|
| 1 | Blank (wheat) | 3.40 | 100 |
| 2 | W Bran cell wall enz (1) | 3.33 | 98 |
| 3 | W Bran cell wall enz + Danisco (2) | 3.88 | 114 |
| 4 | W Bran cell wall enz + Lipopan F (3) | 3.84 | 113 |
| 5 | W Bran cell wall enz + Panamore (4) | 3.91 | 115 |

ID refers to dough composition, number in brackets refers to bran treatment according to table 33. Flour (g) is the amount of flour in the bread. Spec. Vol. (mg/ml) is the absolute specific volumen of the breads. Rel vol vs blank (%) is the relative volume of the breads versus bread 1 (blank).

The resulting breads can be seen in FIG. 9

As can be seen from the above results in experiment 6, a significant effect was obtained on the baking performance in this experiment by combining the cell wall, starch and different lipid modifying enzymes treatment of the bran.

The invention claimed is:

1. A method for the treatment of lipid-containing cereal bran, said method comprising
    a) treating a liquid suspension of a lipid-containing cereal bran with at least one or more enzymes to obtain solubilized cereal bran having a degree of solubilization higher than 1% (dry matter basis); wherein said lipid-containing cereal bran comprises about 1% to about 20% (w/w) of starch, and
    b) treating the liquid suspension of lipid-containing solubilized cereal bran with at least one exogenous phospholipase,
    wherein the treatments are conducted under suitable pH and temperature conditions conducive to said treatments, and
    wherein said treatments produce a treated composition comprising at least 0.05% (dry matter basis) of a solubilized fraction of cereal bran functional lipids.

2. The method according to claim 1, wherein about 1% to about 10% (w/w) of the liquid suspension of lipid-containing cereal bran is starch.

3. The method according to claim 1, wherein steps (a) and (b) are conducted simultaneously.

4. The method according to claim 1 or claim 3, wherein said one or more enzymes used to obtain the solubilized cereal bran comprises one or more cell-wall modifying enzymes.

5. The method according to claim 3, wherein said liquid suspension of lipid-containing cereal bran further contains insoluble cereal bran.

6. The method according to claim 1 or claim 3, wherein said one or more enzymes used to obtain the solubilized cereal bran comprises one or more protease enzymes.

7. The method according to claim 1, wherein said cereal bran is further treated with one or more lipolytic enzymes in addition to treatment with the phospholipase.

8. The method according to claim 1, which method further comprises a step of isolating the soluble fraction.

9. The method according to claim 4, wherein said one or more cell wall modifying enzyme is selected from the group consisting of a xylanase, and a cellulase.

10. The method according to claim 9, wherein said cellulase is selected from an endo-cellulase, an exo-cellulase, a cellobiase, an oxidative cellulases, and a cellulose phosphorylases.

11. The method according to claim 1 or claim 2, wherein said one or more enzymes is a starch modifying enzyme selected from the group consisting of an alpha-amylase, a pullulanase, an isoamylase and a beta-amylase.

12. The method according to claim 1, wherein the lipid-containing cereal bran is provided in particles, wherein the average particle size of said particulate cereal bran is below 3000 μm.

13. The method according to claim 1, wherein the cereal bran is selected from wheat, barley, oat, rye, triticale, rice, and corn.

14. The method according to claim 1, wherein said method further comprises preceding steps of
   i) fractionating a cereal grain to obtain endosperm, bran, and germ;
   ii) separating and distributing the endosperm, bran, and germ to allow them to be treated; and
   iii) milling the bran.

15. The method according to claim 1, wherein said cereal bran is obtained from an industrial milling process and further milled to obtain an average particle size below 500 μm.

16. The method according to claim 1, wherein said lipid-containing cereal bran is a sidestream from processing of cereal bran.

17. The method according to claim 1, wherein said composition comprising functional lipids is further treated to inactivate further enzyme activity.

18. The method according to claim 1, wherein the solubilization degree of said lipid-containing cereal bran obtained prior to said treatment with the phospholipase is higher than 15% (dry matter basis).

19. The method according to claim 1, wherein the total content of solubilized functional lipids in obtained is in the range of 0.05-5% (dry matter basis).

20. The method according to claim 1, wherein said method further comprises a step of drying the composition comprising the solubilized fraction of functional lipids.

21. The method according to claim 1, wherein said method further comprises a step of spray drying the composition comprising the solubilized fraction of functional lipids.

22. The method according to claim 1, wherein said method further comprises a step of lyophilization of the composition comprising the solubilized fraction of functional lipids.

23. The method according to claim 1, wherein said treatment with phospholipase generates functional lipids comprising emulsifiers.

24. The method according to claim 1, wherein said treatment with phospholipase further generates functional sterol esters.

25. The method according to claim 1, wherein said treatment with phospholipase converts more than 5% phosphotidylinositol present in the cereal bran into lysophosphatidylinositol (lyso-PI).

* * * * *